(12) United States Patent
Wilson et al.

(10) Patent No.: US 10,226,476 B2
(45) Date of Patent: Mar. 12, 2019

(54) METHOD OF ATTENUATING REACTIONS TO SKIN IRRITANTS

(71) Applicant: Dana-Farber Cancer Institute, Inc., Boston, MA (US)

(72) Inventors: S. Brian Wilson, Lexington, MA (US); Glenn Dranoff, Lexington, MA (US); Silke Gillessen, St. Gallen (CH)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/802,893

(22) Filed: Jul. 17, 2015

(65) Prior Publication Data

US 2016/0074423 A1 Mar. 17, 2016

Related U.S. Application Data

(60) Continuation of application No. 14/063,356, filed on Oct. 25, 2013, now abandoned, which is a
(Continued)

(51) Int. Cl.
*A61K 31/00* (2006.01)
*A61K 31/685* (2006.01)
(Continued)

(52) U.S. Cl.
CPC ............ *A61K 31/685* (2013.01); *A61K 8/553* (2013.01); *A61K 8/68* (2013.01); *A61K 9/0014* (2013.01);
(Continued)

(58) Field of Classification Search
CPC .... A61K 31/00; A61K 31/133; A61K 31/164; A61K 31/66; A61K 31/661;
(Continued)

(56) References Cited

U.S. PATENT DOCUMENTS 4,885,285 A 12/1989 Baschang et al.
5,445,934 A 8/1995 Fodor et al.
(Continued)

FOREIGN PATENT DOCUMENTS

DE 19841794 A1 3/2000
EP 0988860 A1 3/2000
(Continued)

OTHER PUBLICATIONS

US 5,134,854, 09/1992, Pirrung et al. (withdrawn)
(Continued)

*Primary Examiner* — Ernst V Arnold
(74) *Attorney, Agent, or Firm* — Foley Hoag LLP

(57) ABSTRACT

The present invention is directed to a method of inhibiting CD1d activation by administering a composition containing a moiety that blocks CD1d activation. Compositions of the invention are useful for the attenuation of CD1d-restricted immune responses, including treatment of skin disorders due to hyperactive immune responses (e.g., contact hypersensitivity), for systemic administration to attenuate ongoing immune responses, and to provide hypoallergenic cosmetic products including pharmaceutical, cosmetic, and skin care compositions. Preferably, these compositions are in a form intended for topical administration.

3 Claims, 5 Drawing Sheets

Related U.S. Application Data continuation of application No. 12/146,386, filed on Jun. 25, 2008, now abandoned, which is a division of application No. 10/106,901, filed on Mar. 26, 2002, now Pat. No. 7,419,958.

(60) Provisional application No. 60/278,837, filed on Mar. 26, 2001.

(51) Int. Cl.
```
A61K 8/55        (2006.01)
A61K 8/68        (2006.01)
A61K 31/164      (2006.01)
A61K 31/66       (2006.01)
A61K 31/739      (2006.01)
A61K 31/765      (2006.01)
A61Q 7/00        (2006.01)
A61Q 17/00       (2006.01)
A61Q 19/00       (2006.01)
A61K 31/133      (2006.01)
A61K 31/661      (2006.01)
A61K 31/7028     (2006.01)
C07K 16/28       (2006.01)
A61K 9/00        (2006.01)
A61K 31/7032     (2006.01)
A61K 47/60       (2017.01)
```

(52) U.S. Cl.
CPC ............ *A61K 9/0019* (2013.01); *A61K 31/00* (2013.01); *A61K 31/133* (2013.01); *A61K 31/164* (2013.01); *A61K 31/66* (2013.01); *A61K 31/661* (2013.01); *A61K 31/7028* (2013.01); *A61K 31/7032* (2013.01); *A61K 31/739* (2013.01); *A61K 31/765* (2013.01); *A61K 47/60* (2017.08); *A61Q 7/00* (2013.01); *A61Q 17/00* (2013.01); *A61Q 19/00* (2013.01); *C07K 16/2803* (2013.01); *C07K 16/2896* (2013.01); *C07K 2317/76* (2013.01)

(58) Field of Classification Search
CPC .............. A61K 31/685; A61K 31/7028; A61K 31/7032; A61K 31/739; A61K 31/765; A61K 47/48215; A61K 8/553; A61K 8/68; A61K 9/0014; A61K 9/0019; A61Q 17/00; A61Q 19/00; A61Q 7/00; C07K 16/2803; C07K 16/2896; C07K 2317/76

See application file for complete search history.

(56) References Cited

U.S. PATENT DOCUMENTS

| | | | |
|---|---|---|---|
| 5,498,420 A * | 3/1996 | Mentrup | A61K 8/14 424/401 |
| 5,565,207 A | 10/1996 | Kashibuchi et al. | |
| 5,602,183 A | 2/1997 | Martin et al. | |
| 5,631,734 A | 5/1997 | Stern et al. | |
| 5,679,347 A | 10/1997 | Porcelli et al. | |
| 5,705,187 A | 1/1998 | Unger | |
| 5,776,429 A * | 7/1998 | Unger | A61K 9/127 424/450 |
| 5,776,683 A | 7/1998 | Smith et al. | |
| 5,800,992 A | 9/1998 | Fodor et al. | |
| 5,807,680 A | 9/1998 | Sutcliffe et al. | |
| 5,851,543 A | 12/1998 | Korb et al. | |
| 5,936,076 A | 8/1999 | Higa et al. | |
| 5,945,409 A | 8/1999 | Crandall | |
| 6,086,898 A | 7/2000 | DeKruyff et al. | |
| 6,130,213 A * | 10/2000 | Philippe | A61K 8/14 422/534 |
| 6,143,716 A * | 11/2000 | Meers | A61K 9/127 424/450 |
| 6,197,582 B1 | 3/2001 | Trakht | |
| 6,531,453 B1 | 3/2003 | Taniguchi et al. | |
| 6,555,372 B1 | 4/2003 | Motoki | |
| 6,747,010 B2 | 6/2004 | Taniguchi et al. | |
| 6,800,738 B1 | 10/2004 | Carter et al. | |
| 7,041,870 B2 | 5/2006 | Tomizuka et al. | |
| 7,063,844 B2 | 6/2006 | Porcelli et al. | |
| 7,273,852 B2 | 9/2007 | Tsuji et al. | |
| 7,419,958 B2 | 9/2008 | Wilson et al. | |
| 7,488,491 B2 | 2/2009 | Tsuji et al. | |
| 2001/0051156 A1 | 12/2001 | Zeng et al. | |
| 2002/0009465 A1 | 1/2002 | Porcelli et al. | |
| 2002/0071842 A1 | 6/2002 | Gumperz et al. | |
| 2002/0115624 A1 | 8/2002 | Behar et al. | |
| 2002/0164331 A1 | 11/2002 | Exley et al. | |
| 2002/0165170 A1 | 11/2002 | Wilson et al. | |
| 2002/0171522 A1 | 11/2002 | Kazmierczak | |
| 2002/0171526 A1 | 11/2002 | Laskaris et al. | |
| 2002/0171527 A1 | 11/2002 | Minami et al. | |
| 2002/0171538 A1 | 11/2002 | Su et al. | |
| 2002/0171557 A1 | 11/2002 | Wegener | |
| 2002/0172677 A1 | 11/2002 | Lahn et al. | |
| 2002/0199213 A1 | 12/2002 | Tomizuka et al. | |
| 2003/0064967 A1 | 4/2003 | Luchoomun et al. | |
| 2003/0139351 A1 | 7/2003 | Taniguchi et al. | |
| 2003/0147865 A1 | 8/2003 | Salomon et al. | |
| 2003/0157135 A1 | 8/2003 | Tsuji et al. | |
| 2003/0206914 A1 | 11/2003 | Porcelli et al. | |
| 2004/0009594 A1 | 1/2004 | Wakasugi | |
| 2004/0022913 A1 | 2/2004 | Watson et al. | |
| 2004/0073957 A1 | 4/2004 | Tomizuka et al. | |
| 2004/0087485 A1 | 5/2004 | Iian et al. | |
| 2004/0127429 A1 | 7/2004 | Tsuji | |
| 2004/0171522 A1 | 9/2004 | Ilan et al. | |
| 2004/0171526 A1 | 9/2004 | Ilan et al. | |
| 2004/0171527 A1 | 9/2004 | Ilan et al. | |
| 2004/0171528 A1 | 9/2004 | Ilan et al. | |
| 2004/0171557 A1 | 9/2004 | Iian et al. | |
| 2004/0235162 A1 | 11/2004 | Sato | |
| 2005/0032210 A1 | 2/2005 | Sato et al. | |
| 2005/0159365 A1 | 7/2005 | Serizawa et al. | |
| 2006/0116332 A1 | 6/2006 | Strober et al. | |
| 2007/0104776 A1 | 5/2007 | Ishii et al. | |
| 2008/0241174 A1 | 10/2008 | Umetsu et al. | |
| 2008/0260680 A1 | 10/2008 | Wilson et al. | |
| 2010/0197613 A1 | 8/2010 | Strober et al. | |
| 2011/0038860 A1 | 2/2011 | Zeng et al. | |

FOREIGN PATENT DOCUMENTS

| | | | |
|---|---|---|---|
| EP | 0751780 B1 | 9/2003 | |
| EP | 1767216 A1 | 3/2007 | |
| JP | 63255213 | 10/1988 | |
| JP | 03017020 | 1/1991 | |
| JP | 08116971 A | 5/1996 | |
| JP | H08116971 A | 5/1996 | |
| JP | 11302155 A2 | 11/1999 | |
| JP | 2000264825 A2 | 9/2000 | |
| JP | 2000264829 A2 | 9/2000 | |
| JP | 5331049 B2 | 10/2013 | |
| WO | WO-92/17189 A1 | 10/1992 | |
| WO | WO-95/00163 A1 | 1/1995 | |
| WO | WO-95/35505 A1 | 12/1995 | |
| WO | WO-99/29293 A1 | 6/1999 | |
| WO | WO-99/33475 A1 | 7/1999 | |
| WO | WO-99/41266 A1 | 8/1999 | |
| WO | WO-00/02923 A1 | 1/2000 | |
| WO | WO 0002583 * | 1/2000 | ............ A61K 39/00 |
| WO | WO-01/94949 A2 | 12/2001 | |
| WO | WO-01/94949 A3 | 12/2001 | |
| WO | WO-02/051986 A2 | 7/2002 | |
| WO | WO-02/051986 A3 | 7/2002 | |
| WO | WO-2003/092615 A2 | 11/2003 | |
| WO | WO-2003/092615 A3 | 11/2003 | |
| WO | WO-2004/001655 A1 | 12/2003 | |
| WO | WO-2004/019900 A1 | 3/2004 | |
| WO | WO-2004/028475 A2 | 4/2004 | |

(56) References Cited

FOREIGN PATENT DOCUMENTS

| | | |
|---|---|---|
| WO | WO-2004/028475 A3 | 4/2004 |
| WO | WO-2004/084874 A2 | 10/2004 |
| WO | WO-2004/084874 A3 | 10/2004 |
| WO | WO-2004/094444 A1 | 11/2004 |
| WO | WO-2005/014008 A2 | 2/2005 |
| WO | WO-2005/014008 A3 | 2/2005 |
| WO | WO-2005/032462 A2 | 4/2005 |
| WO | WO-2005/032462 A3 | 4/2005 |
| WO | WO-2005/120574 A1 | 12/2005 |

OTHER PUBLICATIONS

Gumperz et al. (Immunity 2000;21:211-221).*
Chien et al. (Abstract of: Pediatrics 1990; 86(6):4 pages).*
Naidenko et al. (J. Exp. Med. 1999; 190(8):1069-1079).*
Chiu et al. (Biochemica et Biophysica Acta. 2001;1510:56-69).*
Belsito et al. (Biophysical Journal Mar. 15, 2000;78:1420-1430).*
Nikolova et al. (BBA 1996;1305:120-128). (Year: 1996).*
Abcam, 2011 abcam.com/CD1d-antibody-NOR3-2-ab93296.
Abstract: Derwent-ACC-No: 1996-280770 abstracting JP 08116971 A.
Adelman et al., "Treatment of (NZM x NZW)F1 Disease with Anti-1-A Monoclonal Antibodies," J Exp Med, 158(4): 1350-1355 (1982).
Adley et al., "Expression of CD1d in Human Scalp Skin and Hair Follicles: Hair Cycle Related Alterations," J Clin Pathol, 58(12): 1278-1282 (2005).
Akbari et al., "CD4+ Invariant T-cell-receptor+ Natural Killer T Cells in Bronchial Asthma," N Engl J Med, 354(11): 1117-1129 (2006).
Akbari et al., "Essential Role of NKT Cells Producing IL-4 and IL-13 in the Development of Allergen-induced Airway Hyperreactivity," Nat Med, 9(5): 582-588 (2003).
Akbari et al., "Pulmonary Dendritic Cells Producing IL-10 Mediate Tolerance Induced by Respiratory Exposure to Antigen," Nat Immunol, 2(8): 725-731 (2001).
Amano et al., "CD1 Expression Defines Subsets of Follicular and Marginal Zone B Cells in the Spleen: Beta 2-Microglobulin-Dependent and Independent Forms," J Immunol, 161(4): 1710-1717 (1998).
Amoura et al., "Presence of Antinucleosome Autoantibodies in a Restricted Set of Connective Tissue Diseases: Antinucleosome Antibodies of the IgG3 Subclass are Markers of Renal Pathogenicity in Systemic Lupus Erythermatosus," Arthritis Rheum, 43(1): 76-84 (2000).
Anderson, "Endotyping Asthma: New Insights into Key Pathogenic Mechanisms in a Complex, Heterogeneous Disease," Lancet, 372(9643): 1107-1119 (2008).
Ando et al., "Mechanisms of T and B Cell Collaboration in the in Vitro Production of anti-DNA Antibodies in the NZB/NZW F1 Murine SLE Model," J Immunol, 138(10): 3185-3190 (1987).
Apostolou et al., "Murine natural killer cells contribute to the granulomatous reaction caused by mycobacterial cell walls," Proc Natl Acad Sci, 96: 5141-5146 (1999).
Araujo et al., "Exacerbates Th2-mediated Airway Inflammation and Hyperresponsiveness in Autoimmune Diabetes-prone NOD Mice: A Critical Role for CD1d-dependent NKT Cells," Eur J Immunol, 34(2): 327-335 (2004).
Ausubel et al., "Current Protocols in Molecular Biology," New York, NY: John Wiley and Sons Inc.; 1987 (Table of Contents).
Bashyam, "Th1/Th2 Cross-Regulation and the Discovery of IlL-10," J Exp Med, 204(2): 237 (2007).
Bendig et al., "Humanization of Rodent Monoclonal Antibodies by CDR Grafting," Methods-Companion to Methods in Enzymology, 8: 83-93 (1995).
Berkow et al., "The Merck Manual of Diagnosis and Therapy," Merck Research Laboratories, 16: 1316-1321 (1992).

Bilenki et al., "Natural Killer T Cells Contribute to Airway Eosinophilic Inflammation Induced by Ragweed Through Enhanced IL-4 and Eotaxin Production," Eur J Immunol, 34(2): 345-354 (2004).
Blumberg et al., "Expression of a Nonpolymorphic MHC Class I-like Molecule, CD1D, by Human Intestinal Epithelial Cells," The Journal of Immunology, 147: 2518-2524 (1991).
Blumberg et al., "Structure and Function of the CD1 Family of MHC-like Cell Surface Proteins," Immunological Reviews, 147(1): 5-29 (1995).
Boniface et al., "Assessment of T Lymphocyte Cytokine Production in Induced Sputum From Asthmatics: A Flow Cytometry Study," Clin Exp Allergy, 33(9): 1238-1243 (2003).
Bonish et al., "Overexpression of CD1d by Keratinocytes in Psoriasis and CD1d-Dependent IFN-γ Production by NK-T Cells," Journal of Immunology, 165: 4076-4085 (2000).
Brightling et al., "Eosinophils in Asthma and Airway Hyper-responsiveness," Am J Respir Critc Care Med, 169(1): 131-132; author reply 132-133 (2004).
Briken et al., "Diversification of CD1 Proteins: Sampling the Lipid Content of Different Cellular Compartments," Semin Immunol, 12(6): 517-525 (2000).
Brossay et al., "Antigen-Presenting Function of Mouse CD1: One Molecule with Two Different Kinds of Antigenic Ligands," Immunol Rev, 163: 139-150 (1998).
Brossay et al., "Mouse CD1 is Mainly Expressed on Hemopoietic-derived Cells," J Immunol, 159(3): 1216-1224 (1997).
Brown et al., "Beta 2-microglobulin-dependent NK1.1+ T Cells Are Not Essential for T Helper Cell 2 Immune Responses," J Exp Med, 184(4): 1295-1304 (1996).
Buschard et al., "Treatment with Sulfatide or Its Precursor, Galactosylceramide, Prevents Diabetes in NOD Mice," Autoimmunity, 34(1): 9-17 (2001).
Chan et al., "Deficiency in Beta(2)-Microglobulin, But Not CD1, Accelerates Spontaneous Lupus Skin Disease While Inhibiting Nephritis in MRL-Fas(Ipr) Mice: an Example of Disease Regulation at the Organ Level," J Immunol, 167(5): 2985-2990 (2001).
Chang et al., "The Synthesis and Biological Characterization of a Ceramide Library," J Am Chem Soc, 124(9): 1856-1857 (2002).
Cheng et al., "Different Patterns of TCR Transgene Expression in Single-Positive and Double-negative T Cells. Evidence for Separate Pathways of T Cell Maturation," J Immunol, 156(10): 3591-3601 (1996).
Compostella et al., "CD1a-binding Glycosphingolipids Stimulating Human Autoreactive T-cells: Synthesis of a Family of Sulfatides Differing in the Acyl Chain Moiety," Tetrahedron, 58(43): 8703-8708 (2002).
Conboy et al., "Quantitative Measurements of Recombinant HIV Surface Glycoprotein 120 Binding to Several Glycosphingolipids Expressed in Planar Supported Lipid Bilayers," J Am Chem Soc, 124(6): 968-977 (2002).
Daikh et al., "Long-term Inhibition of Murine Lupus by Brief Simultaneous Blockade of the B7/CD28 and CD40/gp39 Costimulation Pathways," J Immunol, 159(7): 3104-3108 (1997).
Datta et al., "Induction of Cationic Shift in IgG anti-DNA Autoantibodies. Role of T Helper Cells with Classical and Novel Phenotypes in Three Murine Models of Lupus Nephritis," J Exp Med, 165(5): 1252-1268 (1987).
Datta et al., "Normal Mice Express Idiotypes Related to Autoantibody Idiotypes of Lupus Mice," Proc Natl Acad Sci USA, 80(9): 2723-2727 (1983).
Dighiero et al., High Frequency of Natural Autoantibodies in Normal Newborn Mice,: J Immunol, 134(2): 765-771 (1985).
Disepio et al., "Novel Approaches for the Treatment of Psoriasis," Drug Discovery Today, 4(5): 222-231 (1999).
Ebling et al., "A Peptide Derived from an Autoantibody Can Stimulate T Cells in the (NZB x NZW)F1 Mouse Model of Systemic Lupus Erythematosus," Arthritis Rheum, 36(3): 355-364 (1993).
Ebling et al., "Restricted Subpopulations of DNA Antibodies in Kidney of Mice with Systemic Lupus. Comparison of Antibodies in Serum and Renal Eluates," Arthritis Rheum, 23(4): 392-403 (1980).
Ei-Gabalawy et al., "Why Do We Not Have a Cure for Rheumatoid Arthritis," Arthritis Res, 4(3): 297-301 (2002).

(56) References Cited

OTHER PUBLICATIONS

Elkhal et al., "CD1d restricted natural killer T cells are not required for allergic skin inflammation," J Allergy Clin Immunol, 118: 1363-1368 (2006).
Erlebacher et al., "Ovarian Insufficiency and Early Pregnancy Loss Induced by Activation of the Innate Immune System," Journal of Clinical Investigation, 114(1): 39-48 (2004).
European Search Report for Application No. 5851383.0 dated Jan. 22, 2008.
European Search Report for EP 02723627.2 dated Jun. 22, 2007.
Fayyazi et al., "Expression of IFNγ, coexpression of TNFα and matrix metalloproteinases and apoptosis of T lymphocytes and macrophages in granuloma annulare," Arch Dermatol Res, 291: 485-490 (1999).
Filion et al., "Anti-inflammatory Activity of Cationic Lipids," British Journal of Pharmacology, 122: 551-557 (1997).
Fontenot et al., "Foxp3 Programs the Development and Function of CD4+CD25+ Regulatory T Cells," Nat Immunol, 4(4): 330-336 (2003).
Forestier et al., "Brucella abortus Lipopolysaccharide in Murine Peritoneal Macrophages Acts as a Down-Regulator of T Cell Activation," Journal Immunology, 175: 763-770 (2005).
Freeman et al., "Quantitative RT-PCR: Pitfalls and Potential," Biotechniques, 26(1): 112-122, 124-125 (1999).
Galactocerebroside bovine derived. Sigma-Aldrich product catalogue. Jun. 2, 2011. www.sigmaaldrich.com/catalog/ProductDetail.do?D7=0&N5=SEARCH_CONCAT_PNO%7CBRAND_KEY&N4=C4905%7CSIGMA&N25=0&QS=ON&F=SPEC.
Gibson, "Monitoring the Patietn with Asthma: An Evidence-based Approach," J Allergy Clin Immunol, 106(1 Pt 1): 17-26 (2000).
Godo et al., "Role of Invariant Natural Killer T (iNKT) Cells in Systemic Lupus Erythematosus," Curr Med Chem, 15(18): 1778-1787 (2008).
Haile et al., "Suppression of Immediate and Late Responses to Antigen by a Non-anaphylactogenic Anti-IgE Antibody in a Murine Model of Asthma," Eur Respir J, 13(5): 961-969 (1999).
Hamanaka et al., "A Trial of Galactosylceramide Containing Cream to the Patients with Atopic Skin and Xerosis," Skin Research, 37(5): 619-625 (1995).
Hansen et al., "Allergen-specific Th1 Cells Fail to counterbalance Th2 Cell-Induced Airway Hyperreactivity but Cause Severe Airway Inflammation," J Clin Invest, 103: 175-183 (1999).
Hether et al., "Chemical Composition and Biological Functions of Listeria Monocytogenes Cell Wall Preparations," Infect Immun, 39(3): 1114-1121 (1983).
Hogan et al., "Aeroallergen-induced Eosinophilic Inflammation, Lung Damage, and Airways Hyperreactivity in Mice Can Occur Independently if IL-4 and Allergen-Specific Immunoglobulins," J Clin Invest, 99(6): 1329-1339 (1997).
Hong et al., "Lipid Antigen Presentation in the Immune System: Lessons Learned From CD1 Knockout Mice," Immunol Rev, 169: 31-44 (1999).
Hori et al., "Control of Regulatory T Cell Development by the Transcription Factor Foxp3," Science, 299(5609): 1057-1061 (2003).
Hughes et al., "Therapeutic Antibodies Make a Comeback," Drug Discovery Today, 3(10): 439-442 (1998).
Humbles et al., "A Critical Role for Eosinophils in Allergic Airways Remodeling," Science, 305(5691): 1776-1779 (2004).
Hutloff et al., "ICOS is an Inducible T-Cell Co-Stimulator Structurally and Functionally Related to CD28," Nature, 397(6716): 263-266 (1999).
International Search Report for PCT Application No. PCTUS05/40182 dated Nov. 22, 2006.
International Search Report for PCT Application No. US01/13728 dated Aug. 2, 2001.
International Search Report for PCT Application No. US05/09075 dated Nov. 4, 2005.
International Search Report for PCT Application No. US2002/09378 dated Nov. 21, 2002.
Invitrogen Product Brochure," Advanced RMPI 1640 and D-MEM/F-12 Product News," downloaded from <<http://tools.invitrogen.com/content/sfs/brochures/B12649_bro.pdf>> (2004).
Ito et al., "A comprehensive two-hybrid analysis to explore the yeast protein interactome," PNAS, 97(2): 740-744 (2000).
Jahng et al., "Activation of Natural Killer T Cells Potentiates or Prevents Experimental Autoimmune Encephalomyelitis," J Exp Med, 194(12): 1789-1799 (2001).
Janeway-Travers," Immunobiology—The Immune System in Health and Disease," Current Biology, Ltd./Garland Publishing, Inc., pp. 8:16-8:19 (1994).
Jones et al., "Glowing Jellyfish, Luminescence and a Molecule Called Coelenterazine," Trends Biotechnol, 17(12): 477-481 (1999).
Joyce et al., "Natural Ligand of Mouse CD1d1: Cellular Glycosylphosphatidylinositol," Science, 279(5356): 1541-1544 (1998).
Kallinich et al., "T-cell Co-Stimulatory Molecules: Their Role in Allergic Immune Reactions," Eur Respir J, 29(6): 1246-1255 (2007).
Kaneko et al., "Pathology and protection in nephrotoxic nephritis is determined by selective engagement of specific Fc receptors," J Exp Med, 191(1): 105-114 (2000).
Kawano et al., "CD1d-Restricted and TCR-Mediated Activation of V-Alpha-14 NKT Cells by Glycosylceramides," Science, 278(28): 1626-1629 (1997).
Kim et al., "Asthma is Induced by Intranasal Coadminstration of Allergen and Natural Killer T-cell Ligand in a Mouse Model," J Allergy Clin Immunol, 114(6): 1332-1338 (2004).
Kobayashi et al., "Enhancing effects of α-, β-monoglycosylceramides on natural killer cell activity," Bioorganic and Medicinal Chemistry, 4(4): 615-519 (1996).
Kono et al., "Development of Lupus in BXSB Mice is Independent of IL-4," J Immunol, 164(1): 38-42 (2000).
Korsgren et al., "Natural Killer Cells Determine Development of Allergen-induced Eosinophilic Airway Inflammation in Mice," J Exp Med, 189(3): 553-562 (1999).
Kotzin et al., "Systemic Lupus Erythematosus," Cell, 85(3): 303-306 (1996).
Kronenberg et al., "Right on Target: Novel Approaches for the Direct Visualization of CD1-specific T Cell Responses," Proc Natl Acad Sci USA, 98(6): 2950-2952 (2001).
Kuby, "Immunology," 3rd Edition, W.H. Freeman and Company, 1992, 1994, 1997, pp. 202, 215, 216, 208, 207.
Kupper et al., "Immune and Inflammatory Processes in Cutaneous Tissues," Mechanisms and Speculations, J Clin Invest, 86(6): 1783-1789 (1990).
Leckie et al., "Effects of an Interleukin-5 Blocking Monoclonal Antibody on Eosinophils, Airway Hyper-responsiveness, and the Late Asthmatic Response," Lancet, 356(9248): 2144-2148 (2000).
Lehuen et al., "Overexpression of Natural Killer T Cells Protects Valpha14-Jalpha281 Transgenic Nonobese Diabetic Mice Against Diabetes," J Exp Med, 188(10): 1831-1839 (1998).
Linden, "Role of Interleukin-17 and the Neutrophil in Asthma," Int Arch Allergy Immunol, 126(3): 179-184 (2001).
Lisbonne et al., "Cutting Edge: Invariant V Alpha 14 NKT Cells are Required for Allergen-Induced Airway Inflammation and Hyper-reactivity in an Experimental Asthma Model," J Immunol, 171(4): 1637-1641 (2003).
Louis et al., "The Relationship Between Airways Inflammation and Asthma Severity," Am J Respir Crit Care Med, 161(1): 9-16 (2000).
Maddison, "Autoantibodies in SLE. Disease Associations," Adv Exp Med Biol, 455: 141-145 (1999).
Magnan et al., "Relationships between natural T cells, atopy, IgE levels, and IL□4 production," Allergy, 55: 286-290 (2000).
Maruyama et al., "Prolonged Circulation Time in Vivo of Large Unilamellar Liposomes Composed of Distearoyl Phosphatidylcholine and Cholesterol Containing Amphipathic Poly(ethylene glycol)," Biochim Biophys Acta, 1128: 44-49 (1992).
Matsuda et al., "alpha-Galactosylceramide, a Ligand of Natural Killer T Cells, Inhibits Allergic Airway Inflammation," Am J Respir Cell Mol Biol, 33(1): 22-31 (2005).
Mehlhop et al., "Allergen-induced Bronchial Hyperreactivity and Eosinophilic Inflammation Occur in the Absence of IgE in a Mouse Model of Asthma," Proc Natl Acad Sci USA, 94(4): 1344-1349 (1997).

(56) References Cited

OTHER PUBLICATIONS

Mempel et al., "Comparison of the T Cell Patterns in Leprous and Cutaneous Sarcoid Granulomas. Presence of Valpha24-Invariant Natural Killer T Cells in T-cell-reactive Leprosy Together with a Highly Biased T Cell Receptor Valpha Repertoire," Am J Pathol, 157(2): 509-523 (2000).
Mempel et al., "Natural Killer T Cells Restricted by the Monomorphic MHC Class 1b CD1d1 Molecules Behave Like Inflammatory Cells," J Immunol, 168(1): 365-371 (2002).
Mohan et al., "Nucleosome: A Major Immunogen for Pathogenic Autoantibody-inducing T Cells for Lupus," J Exp Med, 177(5): 1367-1381 (1993).
Morita et al., "Syntheses of alpha, B-monoglycosyceramides and Four Diastereomers of an alpha-galactosylceramide," Bioorganic & Medicinal Chemistry Letters, 5(7): 699-704 (1995).
Nakajima et al., "Preferential Dependence of Autoantibody Production in Murine Lupus on CD86 Costimulatory Molecule," Eur J Immunol, 25(11): 3060-3069 (1995).
Naumov et al., "Activation of CD1d-restricted T Cells Protects NOD Mice From Developing Diabetes by Regulating Dendritic Cell Subsets," Proc Natl Acad Sci USA, 98(24): 13838-13843 (2001).
Nickoloff et al., "Characterization of a T Cell Line Bearing Natural Killer Receptors and Capable of Creating Psoriasis in a SCID Mouse Model System," J Dermatol Sci, 24(3): 212-225 (2000).
Nickoloff et al., "Response of Murine and Normal Human Skin to Injection of Allogeneic Blood-derived Psoriatic Immunocytes: Detection of T Cells Expressing Receptors Typically Present on Natural Killer Cells, including CD94, CD158, and CD161," Arch Dermatol, 135(5): 546-552 (1999).
Nieda et al., "Activation of Human V-Alpha-24NKT cells by Alpha-Glycosylceramide in a CD1d-Restricted and V-Alpha-24TCR- Mediated Manner," Human Immunology, 60: 10-19 (1999).
Nieuwenhuis et al., "CD1d and CD1d-restricted iNKT-cells Play a Pivotal Role in Contact Hypersensitivity," Exp Dermatol, 14(4): 350-358 (2005).
Office Action for U.S. Appl. No. 09/844,544 dated Feb. 12, 2003.
Office Action for U.S. Appl. No. 09/844,544 dated Jan. 30, 2007.
Office Action for U.S. Appl. No. 09/844,544 dated Jul. 31, 2006.
Office Action for U.S. Appl. No. 09/844,544 dated Oct. 21, 2003.
Office Action for U.S. Appl. No. 09/844,544 dated Feb. 6, 2008.
Office Action for U.S. Appl. No. 10/106,901 dated Dec. 17, 2002.
Office Action for U.S. Appl. No. 10/106,901 dated Jan. 6, 2005.
Office Action for U.S. Appl. No. 10/106,901 dated Jul. 24, 2006.
Office Action for U.S. Appl. No. 10/106,901 dated Jun. 26, 2003.
Office Action for U.S. Appl. No. 10/106,901 dated Mar. 22, 2007.
Office Action for U.S. Appl. No. 10/106,901 dated Mar. 31, 2004.
Office Action for U.S. Appl. No. 10/106,901 dated Sep. 19, 2007.
Office Action for U.S. Appl. No. 11/266,033 dated Feb. 6, 2009.
Office Action for U.S. Appl. No. 11/266,033 dated Jun. 25, 2009.
Office Action for U.S. Appl. No. 12/146,386 dated Apr. 12, 2011.
Office Action for U.S. Appl. No. 12/146,386 dated May 1, 2013.
Office Action for U.S. Appl. No. 12/146,386 dated Nov. 17, 2010.
Office Action for U.S. Appl. No. 12/697,882 dated Aug. 15, 2013.
Office Action for U.S. Appl. No. 12/697,882 dated Mar. 4, 2011.
Office Action for U.S. Appl. No. 12/697,882 dated Oct. 20, 2011.
Office Action for U.S. Appl. No. 12/762,091 dated Aug. 26, 2011.
Office Action for U.S. Appl. No. 12/762,091 dated Jul. 17, 2013.
Office Action for U.S. Appl. No. 12/762,091 dated May 7, 2012.
Oishi et al., "Selective Reduction and Recovery of Invariant Valpha24JalphaQ T Cell Receptor T Cells in Correlation with Disase Activity in Patients with Systemic Lupus Erythematosus," J Rheumatol, 28(2): 275-283 (2001). Abstract only.
Ortaldo et al., "Dissociation of NKT Stimulation, Cytokine Induction, and NK Activation in Vivo by the Use of Distinct TCR-binding Ceramides," J Immunol, 172(2): 943-953 (2004).
Panja et al., "Adhesion Molecules are Expressed on Intestinal Epithelial Cells but Do not Participate in T Cell Interactions," Gastroenterology, 100: A606 (1991).
Paquet et al., "Immunopotentiating Activities of Cell Walls, Peptidoglycans, and Teichoic Acids from Two Strains of Listeria Monocytogenes," Infect Immun, 54(1): 170-176 (1986).
Park et al., "Inhibitory Activity of a Ceramide Library on Interleukin-4 Production from Activated T Cells," Bioorg Med Chem, 13(7): 2589-2595 (2005).
Park et al., "Innate and Adaptive Functions of the CD1 Pathway of Antigen Presentation," Semin Immunol, 10(5): 391-398 (1998).
Peltier et al., "Immunology of Term and Preterm Labor," Reprod Biol Endocrin, 1(122): 1-11 (2003).
Rhee et al., "Inhibition of CD1d Activation Suppresses Septic Mortality: A Role for NK-T Cells in Septic Immune Dysfunction," J Surg Res, 115(1): 74-81 (2003).
Rubin et al., "Anti-DNA Activity of IgG F(ab')2 From Normal Human Serum," J Immunol, 122(4): 1604-1607 (1979).
Sachiko Miyake et al., "Potential of Targeting Natural Killer T Cells for the Treatment of Autoimmune Disases," Mod Rheumatology, 14: 279-284 (2004).
Santoro et al., "The Contribution of L3T4+ T Cells to Lymphoproliferation and Autoantibody Production in MRL-Ipr/Ipr Mice," J Exp Med, 167(5): 1713-1718 (1988).
Schuffler et al., "Listeria Cell Wall Fraction. Characterization of in Vitro Adjuvant Activity," Immunology, 31(2): 323-329 (1976).
Sharif et al., "Activation of Natural Killer T Cells by Alpha-galactosylceramide Treatment Prevents the Onset and Recurrence of Autoimmune Type 1 Diabetes," Nat Med, 7(9): 1057-1062 (2001).
Shi et al., "Germ Line Deletion of the CD1 Locus Exacerbates Diabetes in the NOD Mouse," Proc Natl Acad Sci USA, 98(12): 6777-6782 (2001).
Singh et al., "Genetic Deletion of CD1 in Lupus: Evidence of a Regulatory Role," Arth Rheum Suppl, 44: 283 (2001).
Singh et al., "Natural Killer T Cell Activation Protects Mice Against Experimental Autoimmune Encephalomyelitis," J Exp Med, 194(12): 1801-1811 (2001).
Singh et al., "T Cell Determinants from Autoantibodies to DNA Can Upregulate Autoimmunity in Murine Systemic Lupus Erythematosus," J Exp Med ,181(6): 2017-2027 (1995).
Somnay-Wadgaonkar et al., "Immunolocalization of CD1d in Human Intestinal Epithelial Cells and Identification of a Beta2-microglobulin-associated Form," Int Immunol, 11(3): 383-392 (1999).
Stanic et al., "Beta-D-glycosylceramide is a Precursos of an NKT Cell Antigen," FASEB Journal, 16(5): A1237 (2002).
Stock et al., "CD8(+) T Cells Regulate Immune Responses in a Murine Model of Allergen-Induced Sensitization and Airway Inflammation," Eur J Immunol, 34(7): 1817-1827 (2004).
Stock et al., "Induction of T Helper Type 1-like Regulatory Cells that Express Foxp3 and Protect Against Airway Hyper-reactivity," Nat Immunol, 5(11): 1149-1156 (2004).
Sugita et al., "T Lymphocyte Recognition of Human Group 1 CD1 Molecules: Implications for Innate and Acquired Immunity," Semin Immunol, 12(6): 511-516 (2000).
Sumida et al., "Selective Reduction of T Cells Bearing Invariant V Alpha 24J Alpha Q Antigen Receptor in Patients with Systemic Sclerosis," J Exp Med, 182(4): 1163-1168 (1995).
Swain et al., "Monoclonal Antibody to L3T4 Blocks the Function of T Cells Specific for Class 2 Major Histocompatibility Complex Antigens," J Immunol, 132(3): 1118-1123 (1984).
Swain, "T Cell Subsets and the Recognition of MHC Class," Immunol Rev, 74: 129-142 (1983).
Szabo et al., "A Novel Transcription Factor, T-bet, Directs Th1 Lineage Commitment," Cell, 100(6): 655-669 (2000).
Szabo et al., "Distinct Effects of T-bet in TH1 Lineage Commitment and IFN-gamma Production in CD4 and CD8 T Cells," Science, 295(5553): 338-342 (2002).
Takahashi et al., "Natural Killer T Cells and Innate Immune B Cells from Lupus-Prone NZB/W Mice Interact to Generate IgM and IgG Autoantibodies," Eur J Immunol, 38(1): 156-165 (2008).
Taniguchi et al., "Essential Requirement of an Invariant V Alpha 14 T Cell Antigen Receptor Expression in the Development of Natural Killer T Cells," Proc Natl Acad Sci USA, 93(20): 11025-11028 (1996).

(56) References Cited

OTHER PUBLICATIONS

Trautmann et al., "New insights into the role of T cells in atopic dermatitis and allergic contact dermatitis," Trends in Immunology, 22(10): 530-532 (2001).
Tupin et al., "CD1d-dependent Activation of NKT Cells Aggravates Atherosclerosis," The Journal of Experimental Medicine, 199(3): 417-422 (2004).
Umetsu et al., "Regulatory T Cells Control the Development of Allergic Disease and Asthma," J Allergy Clin Immunol, 112(3): 480-487 (2003).
Van der Vliet et al., "Effects of alpha-galactosylceramide (KRN7000), Interleukin-12 and Interleukin-7 on Phenotype and Cytokine Profile of Human Valpha24+ VBeta11 + T Cells," Immunology, 98(4): 557-563 (1999).
Vaughan et al., "Human Antibodies by Design," Nat Biotechnol, 16(6): 535-539 (1998).
Velculescu et al., "Serial Analysis of Gene Expression," Science, 270(5235): 484-487 (1995).
Vijayanand et al., "Invariant Natural Killer T Cells in Asthma and Chronic Obstructive Pulmonary Disease," N Engl J Med, 356(14): 1410-1422 (2007).
Vyse et al., "Backcross Analysis of Genes Linked to Autoantibody Production in New Zealand White Mice," J Immunol, 157(6): 2719-2727 (1996).
Wenzel et al., "Effect of an Interleukin-4 Variant on Late Phase Asthmatic Response to Allergen Challenge in Asthmatic Patients: Results of Two Phase 2a Studies," Lancet, 370(9596): 1422-1431 (2007).
Williams et al., "Mast Cells Can Amplify Airway Reactivity and Features of Chronic Inflammation in an Asthma Model in Mice," J Exp Med, 192(3): 455-462 (2000).
Wofsy et al., "Successful Treatment of Autoimmunity in NZB/NZW F1 Mice with Monoclonal Antibody to L3T4," J Exp Med, 161(2): 378-391 (1985).
Wollenberg et al., "Atopic dermatitis: from the genes to skin lesions," Allergy, 55: 205-213 (2000).
Yang et al., "Immunoregulatory Role of CD1d in the Hydrocarbon Oil-Induced Model of Lupus Nephritis," J Immunol, 171(4): 2142-2153 (2003).
Yang et al., "Repeated Alpha-Galactosylceramide Adminstration Results in Expansion of NK T Cells and Alleviates Inflammatory Dermatitis in MRL-Ipr/Ipr Mice," J Immunol, 171(8): 4439-4446 (2003).
Yoshimoto et al., "Nonredundant Roles for CD1d-restricted Natural Killer T Cells and Conventional CD4+ T Cells in the Induction of Immunoglobulin E Antibodies in Response to Interleukin 18 Treatment of Mice," J Exp Med, 197(8): 997-1005 (2003).
Zeng et al., "Activation of Natural Killer T Cells in NZB/W Mice Induces Th1-Type Immune Responses Exacerbating Lupus," J Clin Invest, 112(8): 1211-1222 (2003).
Zeng et al., "Cutting Edge: A Role for CD1 in the Pathogenesis of Lupus in NZB/NZW Mice," J Immunol, 164(10): 5000-5004 (2000).
Zeng et al., "Granulocyte Colony-Stimulating Factor Reduces the Capacity of Blood Mononuclear Cells to Induce Graft-Versus-Host Disease: Impact on Blood Progenitor Cell Transplanation," Blood, 90(1): 453-463 (1997).
Zeng et al., "Subsets of Transgenic T Cells that Recognize CD1 Induce or Prevent Murine Lupus: Role of Cytokines," J Exp Med, 187(4): 525-536 (1998).
Zhang et al., "Beta 2-microglobulin-dependent T Cells Are Dispensable for Allergen-Induced T Helper 2 Responses," J Exp Med, 184(4): 1507-1512 (1996).
Zhou et al., "A Distinct Pattern of Cytokine Gene Expression by Human CD83+ Blood Dendritic Cells," Blood, 86(9): 3295-3301 (1995).

\* cited by examiner

METHOD OF ATTENUATING REACTIONS TO SKIN IRRITANTS

CROSS-REFERENCE

This application is a Continuation Application of U.S. patent application Ser. No. 14/063,356, filed Oct. 25, 2013; which is a Continuation Application of U.S. patent application Ser. No. 12/146,386, filed Jun. 25, 2008; which is a Divisional Application of U.S. patent application Ser. No. 10/106,901, filed Mar. 26, 2002, now U.S. Pat. No. 7,419,958; which claims the benefit of U.S. Provisional Patent Application No. 60/278,837, filed Mar. 26, 2001, each of which is entirely incorporated herein by reference.

This invention was supported by National Institutes of Health Grants R01 AI45051, K11 DK02345, and R01 CA74886 and the government of the United States has certain rights thereto.

FIELD OF THE INVENTION

The present invention is directed to a method of attenuating and/or inhibiting a variety of reactions such as rashes caused by irritants. Preferably, the attenuated reaction is an immune response associated with CD1d activation.

BACKGROUND OF THE INVENTION

The skin represents the body's initial line of defense against the environment. The body is continually exposed to a barrage of molecules, many of which can cause an adverse reaction upon contact. These reactions can follow a spectrum from causing a dramatic and detrimental effect on an individual to skin discoloration and blotching.

The reactions include typical allergic dermatitis, including contact dermatitis and atopic dermatitis, as well as irritant dermatitis.

Contact dermatitis is an inflammation of the skin, which occurs when the skin comes in contact with substances that the skin is sensitive or allergic to. The reaction usually appears within 24-48 hours after exposure to the allergen. Common symptoms include redness, itching and swelling. Sometimes blistering and weeping of the skin also develop. The clinical symptoms of contact dermatitis can include acute eczema accompanied by erythema, edema, papula, vesicle, erosion, and itching. Repeated exposure to an irritant can lead to the development of eczema accompanying lichenification and infiltration. Allergic contact dermatitis can appear after initial or prolonged exposure to an irritant. Contact dermatitis includes irritant dermatitis, phototoxic dermatitis, allergic dermatitis, photoallergic dermatitis, contact urticaria, systemic contact-type dermatitis and the like.

A wide range of agents can cause allergic contact dermatitis including for example, metals (e.g. nickel, chromium, cobalt), fragrances, chemicals, cosmetics, textiles, pesticides, plastics, and pollen (see, for example, R. J. G. Rycroft et al. "Textbook of Contact Dermatitis").

Therapeutic agents such as drugs may also cause allergic contact dermatitis, particularly when administered transdermally. It is well known that many drugs, e.g., topical ointments, including some currently marketed in the United States (e.g. clonidine) sensitize the skin when used.

Skin sensitization may be produced not only by transdermally delivered drugs, but also by a non-sensitizing drug combined with skin sensitizing permeation enhancers, or a combination of a sensitizing drug and a sensitizing permeation enhancer. Penetration of these sensitizing agents into the skin and the resulting adverse reaction of the skin may persist well beyond the time that the transdermal patch is removed from the skin. The reaction of the skin may be a source of discomfort and a clinical complication in patients suffering from such a reaction.

Atopic dermatitis is developed by exposure to various antigens, since an individual has an atopic disposition which is hypersensitivity against a certain substance. The clinical symptoms include marked itching, skin hypertrophy, infiltration, lichenification and the like.

Irritant dermatitis can occur when too much of a substance is used on the skin or when the skin is sensitive to a certain substance. Susceptibility can include a genetic component. Skin-irritating agents are substances (e.g. soap) that cause an immediate and generally localized adverse response. The response is typically in the form of redness and/or inflammation and generally does not extend beyond the immediate area of contact. Symptoms that are commonly seen include redness, scaling, and the skin looking irritated and sore.

Psoriasis is a skin condition associated with hyper-proliferation of skin cells and immunologic involvement. Psoriasis is a common, idiopathic chronic skin disease characterized by inflamed, scaling, skin lesions containing infiltrates of neutrophils, lymphocytes, and monocytes. Psoriasis manifests in many forms, including cutaneous, mucosal, ungual, and even psoriatic rheumatism. The most effective treatment in the control of localized psoriasis for most patients is the use of topical corticosteroids and topical coal-tar preparations. With certain patients who have generalized psoriasis, it has been necessary to use a variety of systemic chemotherapeutic agents, especially methotrexate.

Certain irritants may cause both allergic and non-allergic contact dermatitis. For example, latex. Latex refers to a type of plastic made from the milky sap of the rubber tree, and contains many proteins which can cause allergic reactions in sensitive individuals. Symptoms can range from watery eyes, hives, rash, swelling, wheezing and in severe cases, anaphylaxis. These responses can occur when latex items touch the skin; the mucous membranes (including the mouth, bladder, genitals, or rectum), and open wounds or bloodstream (especially during surgery). Anybody can develop latex sensitivity. People at increased risk for developing latex allergy include workers with ongoing latex contact (like health care workers), persons with many environmental allergies (hay fever), and those with spina bifida. Latex is found in a wide array of common products, including, for example: gloves, balloons, band-aids, tourniquets, bandages, catheters, rubber bands, IV, other tubing (ex. stethoscopes), art supplies, pacifiers, bottle nipples, diapers, condoms/diaphragms, elastic, chewing gum, carpeting, hand grips of bicycles and motorcycles, shoe soles, auto tires, swimming goggles and equipment.

The more common reaction to latex products is not allergic, but rather, irritant contact dermatitis, which can cause dry, itchy, irritated areas on the skin, usually the hands. Skin reactions include a rash that usually begins 24 to 48 hours after contact. It may progress to oozing blisters or spread away from area touched by latex. Latex allergy (immediate hypersensitivity) is a more serious reaction. Certain proteins in latex cause an allergic reaction. The amount of exposure needed to cause symptoms is not known. Very low levels of exposure can trigger allergic reactions in some people, while having no affect to most people. Reactions usually begin within minutes of exposure to latex, but can occur hours later and have a variety of symptoms. Mild reactions to latex usually cause skin redness, hives, or itching. More severe reactions can cause respiratory or breathing symptoms such as runny nose, sneezing, itchy eyes, scratchy throat, and asthma (trouble breathing, coughing, and wheezing).

Individuals can also develop allergic dermatitis and/or irritant dermatitis in response to insects and plants and shrubbery. For example, certain plants such as poison ivy excrete chemicals that upon contact can cause adverse reactions in humans. These reactions may particularly occur during gardening or nature walks.

Many animals can also suffer from a variety of skin irritations and inflammations generally known as dermatitis. For example, all animals can develop contact dermatitis caused by flea, mosquito, or other insect bites, allergies, external stimulation such as from prickly plants, and for other reasons. The condition has been notoriously difficult to treat. Veterinarians occasionally resort to injections of various medicines in an attempt to alleviate the symptoms and cure the dermatitis.

Presently known therapies for treating or preventing reactions associated with such irritants are inadequate. For example, steroidal agents and antihistamine agents have been used as therapeutic agents for contact dermatitis, and these and a part of the so-called anti-allergic agents have been used for atopic dermatitis. The most widely prescribed drugs to treat dermatologic disease are corticosteroids, also known as glucocorticosteroids or glucocorticoids. Approximately 50% of prescriptions written by dermatologists are for topical corticosteroids. However, these drugs can cause adverse reactions and/or are not fully effective. Systemic corticosteroids are often required in some severe dermatologic diseases but topical treatment is preferred in most responsive cases because it causes fewer systemic adverse effects.

Individual topical corticosteroid preparations vary in anti-inflammatory potency and clinical efficacy.

Though some steroids, particularly mid- to high-potency steroids, are efficacious in chronic dermatoses, long term use of steroids is associated with serious local side effects. These include skin atrophy (thinning, telangiectasia, striae) and a prompt rebound flare when the steroid is stopped. Treatment of large areas of skin and use of occlusive dressings can also increase the potential for adverse effects. This is especially the case in children.

Examples of anti-histamine agents include diphenhydramine hydrochloride, mequitazine, promethazine hydrochloride, and chlorpheniramine maleate anti-histamines have been used mainly to reduce itchiness. Anti-allergic agents include tranilast, ketotifen fumarate, oxatomide, and azelastine hydrochloride. In general, conventional so-called antiallergic agents are either ineffective or fail to show satisfactory therapeutic effects on contact dermatitis and atopic dermatitis.

Accordingly, there is a need for a treatment for skin reactions including allergic dermatitis (contact dermatitis and atopic dermatitis), as well as irritant dermatitis.

The pathophysiologic mechanisms involved in the above-described skin disorders and the evolution of such inflammatory processes are poorly understood. There are numerous skin conditions characterized by increased T cell activation and abnormal antigen presentation in the dermis and epidermis. Thus, there has been speculation that skin cells are important in the generation of a cutaneous inflammatory response (Kupper, "Immune and Inflammatory Processes in Cutaneous Tissues", J. Clin. Invest., 86, pp. 1783-89 (1990)).

CD1d-restricted NK T cells are among the immune system cells found in the skin. The in vivo functions of CD1d-restricted NK T cells are not fully known. They are involved in the IgG response to GPI-anchored proteins of various parasites, contribute to the IL-12-mediated rejection of tumors, and appear to regulate some autoimmune disorders and clearance of certain infections through the production of cytokines. Many of these functions have been observed by using lipid ligands that bind CD1d and activate NK T cells. For example, α-gal-cer.

In humans, the direct cellular targets for their immunomodulatory function(s) have remained enigmatic.

SUMMARY OF THE INVENTION

We have now discovered that one can attenuate and block CD1d activation. This can be done by administering compositions that attenuate CD1d-restricted NK T cell responses. Such compositions include compounds that act as antagonists by binding CD1d and inhibiting activation of CD1d-restricted NK T cells, compounds that block CD1d-specific receptors on NK T cells, and decoys, mimics and the like. Compositions include pharmaceutical and cosmetic compositions.

One preferred group of compositions include phospholipids that bind CD1d without activating NK T cells. Preferred phospholipids include 1,2-Dipalmitoyl-sn-Glycero-3-Phosphoethanolamine (DPPE) and 1,2-Dipalmitoyl-sn-Glycero-3-Phosphoethanolamine-N-[Poly(ethylene glycol) 2000](DPPE-PEG).

Another preferred group of compositions includes glycolipid antagonists that bind CD1d without activating NK T cells. Preferred glycolipids include ceramide, αMan Cer, and βGal Cer.

Another preferred group of compositions includes phosphatidyl inositol.

This method of attenuating CD1d activation can be used for treatment of conditions associated with activation of CD1d-restricted NK T cells. Preferred conditions include skin disorders due to hyperactive CD1d-restricted T cell responses and other disorders associated with ongoing CD1d-restricted immune responses.

Such CD1d associated skin disorders include contact dermatitis and further eczematous dermatitises, atopical dermatitis, seborrheic dermatitis, psoriasis, Lichen planus, Pemphigus, bullous Pemphigoid, epidermolysis bullosa, urticaria, angioedemas, vasculitides, erythemas, cutaneous eosinphilias, Lupus erythematosus, and Alopecia areata.

A preferred embodiment of the invention is directed to the treatment of contact hypersensitivity.

Another embodiment of the invention provides hypoallergenic cosmetic products.

Another embodiment of the invention is directed to compositions that can be used prophylactically to prevent a reaction before one encounters the irritant. For example, a composition to use before weeding.

One preferred embodiment of the invention provides preventing or treating skin sensitization produced by topical administration of therapeutic drugs.

Other embodiments of the invention provide systemic administration of compositions to attenuate ongoing CD1d-restricted immune responses. Systemic therapy can be used in any individual for which activation of NKT cells would be adverse. Systemic conditions can include individuals with autoimmune disease such as lupus. It can also be used in women at high risk for spontaneously aborting pregnancies.

In one embodiment of the invention, a locally administrable topical pharmaceutical or cosmetic composition is provided for the attenuation or treatment of skin conditions associated with CD1d-restricted immune responses. The locally administrable topical pharmaceutical composition includes a topical carrier.

DETAILED DESCRIPTION OF THE INVENTION

The present invention is directed to a method of inhibiting CD1d activation. The method comprises administering a composition containing a moiety that blocks CD1d activation.

Compositions of the invention are useful for the attenuation of CD1d-restricted immune responses, including treatment of skin disorders due to hyperactive immune responses (e.g., contact hypersensitivity), for systemic administration to attenuate ongoing immune responses, and to provide hypoallergenic cosmetic products including pharmaceutical, cosmetic, and skin care compositions. Preferably, these compositions are in a form intended for topical administration.

We have discovered that certain antagonists bind CD1d and inhibit activation of NK T cells. Consequently, by exposing CD1d-expressing cells to a CD1d-specific antagonist, one can attenuate immune responses by specific inhibition of CD1d-restricted events. Antagonists of the present invention include any molecules that inhibit activation of CD1d-restricted NK T cells. Thus, one can treat subjects suffering from an activated CD1d associated disorder such as a skin disorder by administering an effective amount of CD1d specific antagonist.

Such compounds include antagonists that bind CD1d and inhibit NK T cell activation, antagonists that block CD1d-specific receptors such as on NK T cells, decoys that prevent CD1d binding to the CD1d specific receptor, and the like.

Experiments in human models have revealed that CD1d-restricted CD161+ T cells specifically target myeloid dendritic (DC1) cells. DC1 dendritic cells are integral to the genesis of Th1 immune responses. Accordingly, their susceptibility to lysis by CD1d-restricted CD161+ T cells may be part of a negative feedback loop in cell-mediated immune responses.

Figure 1:
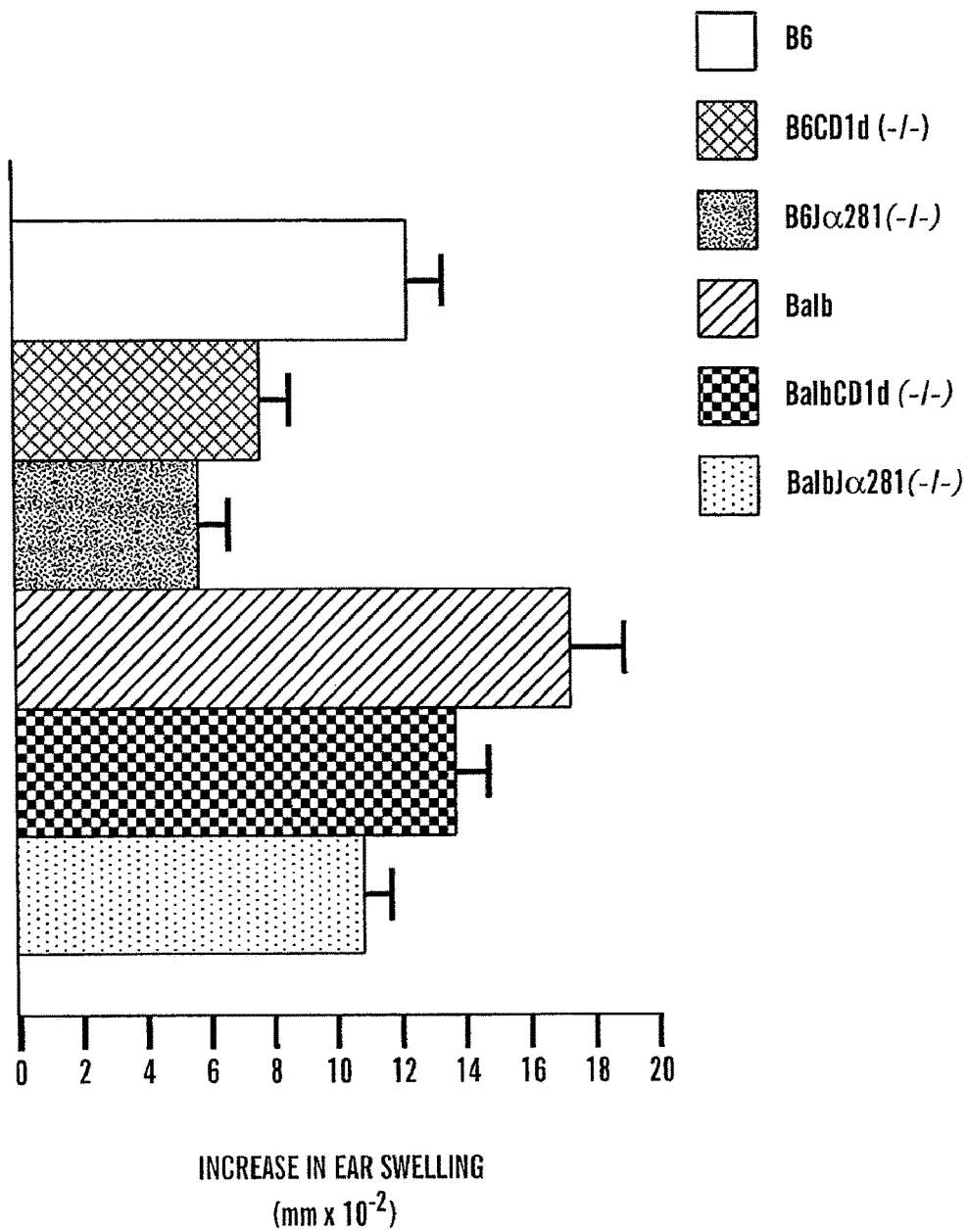
FIG. 1 is a graph showing that contact hypersensitivity is ablated in Cd1d knock out mice and in iNKT cell knock out mice. Mice at least seven weeks of age were sensitized epicutaneously on day 0 with 150 µl of 3% oxazolone in 100% ethanol on the shaved abdomen. 6 days later the right ear was challenged with 1% oxazolone, 10 µl on each side or carrier only. The hapten specific increase in ear thickness at 24 hours was determined using a micrometer.

We tested dendritic cell function in CD1d null and wild type mice. The CD1d mull mice had impaired priming responses in mixed lymphocyte reactions, to tumor vaccinations, and in skin contact hypersensitivity (see FIG. 1). In addition, contact hypersensitivity could be blocked by the cutaneous addition of lipid ligands know to bind CD1d but not activate NK T cells (see FIG. 2).

Accordingly, one can readily determine whether a compound inhibits activation of CD1d by looking at activation of CD1d-restricted NK T cells in vitro using standard assays such as described herein. For example, the proliferation of NK T cells is indicative of their activation by binding to CD1d-expressing cells. Proliferation can be measured, for example, by determining the incorporation of [$^3$H]thymidine into Vα14 NK T cells (Kawano et al., Science 278:1626-29 (1997)). Other in vitro assays include the induction of cytokine production.

CD1d-specific antagonists include any antagonist that binds CD1d and inhibits activation of NK T cells. The binding of an antagonist to CD1d can be determined in vitro using standard assays. For example, surface plasmon resonance (Naidenko et al., J. Exp. Med. 190:1069-79 (1999)). Molecules known to bind CD1d include antibodies, phospholipids and glycolipids, including highly glycosylated sphingolipids (gangliosides) (Kawano et al., Science 278: 1626-9 (1997); Naidenko et al., J. Exp. Med. 190:1069-79 (1999); Briken et al., Sem. Immunol. 12: 517-25 (2000); Kronenberg et al., Proc. Natl. Acad. Sci. USA 98: 2950-52 (2001)).

Phospholipids that bind CD1d without activating NK T cells include 1,2-Dipalmitoyl-sn-Glycero-3-Phosphoethanolamine (DPPE) (Naidenko et al., 1999). The phospholipid may be coupled to a conjugate, such as other lipids coupled to a carrier such as biotin or a poly(alkaline oxide), for example polyethylene glycol (PEG). Polymeric substances such as dextran, polyvinyl pyrrolidones, polysaccharides, starches, polyvinyl alcohols, polyacryl amides or other similar polymers can be used. Polyethylene glycol (PEG) as the poly(alkylene oxide) is preferred. The poly(alkylene oxides) can include monomethoxy polyethylene glycol, polypropylene glycol, block copolymers of polyethylene glycol and polypropylene glycol and the like. The polymers can also be distally capped with $C_{1-4}$ alkyls instead of monomethoxy groups.

Other preferred phospholipids include phosphatidyl inositol.

Glycolipids that bind to CD1d share a common motif consisting of a hydrophobic portion composed of a branched or dual alkyl chain moiety with a covalently linked hydrophilic cap formed by a polar or charged group of the lipid of associated carbohydrates (Briken et al., 2000). The prototypical glycolipid antigen presented by CD1d is -galactosylceramide (Kawano et al., 1997). Thus, D1d antagonists can include glycolipids such as monoglycosylated ceramides and diglycosylated ceramides (Kawano et al., 1997).

Examples of monoglycosylated ceramides and diglycosylated ceramides which bind CD1d but do not activate NK T cells can include ceramides with inner sugar groups at the β-anomer position (such as Galα1-4Glcβ1-1'Cer), an axial configuration of the 2-hydroxyl group (such as α-ManCer), derivatives lacking the 3- and 4-hydroxyl groups on the phytosphingosine of α-GalCer (such as 3,4-deoxy α-GalCer), and ceramides with fatty acyl chain with less than $C_{26}$, and a sphingosine base less than $C_{18}$. Glycolipid antagonists can also be coupled to a conjugate such as biotin or a poly(alkylene oxide), for example PEG.

Other CD1d glycolipid antagonists include highly glycosylated sphingolipids, also known as gangliosides. Ganglioside antagonists include GM1 and GD1a (Naidenko et al., 1997). The antagonists can be coupled to a conjugate such as a biotin or poly(alkylene oxide).

Preferred examples of CD1d-specific lipid antagonists include but are not limited to: DPPE-PEG, phosphatidyl inositol, ceramide, α-ManCer, β-GalCer, Galα1-4Glcβ1-1'Cer, and 13,4-deoxy α-GalCer, GM1, and GD1a.

Other antagonists can include antibodies that specifically bind to CD1d and in doing so prevent CD1d from binding to a CD1d specific receptor. Single chain antibodies and humanized monoclonal antibodies are preferred. Alternatively, one can use molecules that block the CD1d-specific receptor. For example, a molecule. Alternatively, one can modify the lipids that activate CD1d binding by capping the end that bind to CD1d (Kawano et al., *Science* 278: 1626-9 (1997); Naidenko et al., *J. Exp. Med.* 190:1069-79 (1999); Briken et al., *Sem. Immunol.* 12: 517-25 (2000); Kronenberg et al., *Proc. Natl. Acad. Sci. USA* 98: 2950-52 (2001)).

One can also use decoys that mimic CD1d receptors so that the CD1d molecule does not bind to the receptor.

CD1d blocking molecules are presently preferred.

Compositions of the invention should be physiologically stable at therapeutically effective concentrations. Physiological stable compounds are compounds that do not break down or otherwise become ineffective upon introduction to a patient prior to having a desired effect. Compounds are structurally resistant to catabolism, and thus, physiologically stable, or coupled by electrostatic or covalent bonds to specific reagents to increase physiological stability. Such reagents include amino acids such as arginine, glycine, alanine, asparagine, glutamine, histidine or lysine, nucleic acids including nucleosides or nucleotides, or substituents such as carbohydrates, saccharides and polysaccharides, lipids, fatty acids, proteins, or protein fragments. Useful coupling partners include, for example, glycol such as polyethylene glycol, glucose, glycerol, glycerin and other related substances.

Preferably, the compositions are not substantially toxic, myelotoxic, mutagenic or teratogenic at required dosages. Although side effects may occur, preferably the benefits achieved from their use outweigh disadvantages attributable to adverse side effects.

Compositions of the present invention can be used to prevent or treat any condition associated with activation of CD1d-restricted NK T cells, in which attenuation of CD1d activation, such as attenuation of the CD1d-restricted NK T cell response, would be desirable. Preferred embodiments of the invention include topical administration to treat skin disorders due to hyperactive immune responses (e.g., contact hypersensitivity) and systemic administration. Prophylactic use to attenuate immune responses. For example, to avoid reactions to certain plants such as poison ivy, poison oak, etc. when you are going to be in an area where exposure to such a substance is likely, for example, if you are going to be in the woods, gardening, etc.

Systemic administration is preferred in any individual for which activation of NKT cells would be adverse.

Certain women have a problem with spontaneous abortion which appears to be associated with high levels of CD1d. These individuals could use the present compositions before trying to conceive, preferably using systemic administration.

Certain individuals with autoimmune diseases have complications associated in part with CD1d activation. These compositions can be used with such individuals.

One problem with allergic or irritant caused itching is that the scratching can in fact result in further irritation that causes rashes and irritation long after the initial stimulus is gone. This is a particular problem with non-human animals. These compositions can be used to attenuate, treat or present such conditions. Another preferred embodiment includes the composition in hypoallergenic cosmetic products.

In one embodiment of the invention, a locally administrable topical pharmaceutical composition is provided for the prevention or treatment of skin conditions associated with CD1d-restricted T cell responses. Skin conditions include, but are not limited to, contact dermatitis and further eczematous dermatitises, atopical dermatitis, seborrheic dermatitis, Lichen planus, Pemphigus, bullous Pemphigoid, epidermolysis bullosa, urticaria, angioedemas, vasculitides, erythemas, cutaneous eosinphilias, Lupus erythematosus, and Alopecia areata.

A preferred skin condition is contact dermatitis. Contact dermatitis can be caused by a variety of irritants. The most widely known natural allergens which are capable of sensitizing and causing contact dermatitis in many people are antigenic plants of the genus *Rhus*, such as poison ivy, poison oak, and poison sumac. Other widely known skin irritants are commercial products such as insecticides containing Pyrethrum or Rotenone, dye intermediates such as aniline, nitro compounds, anthracene, and derivatives thereof, dyes such as paraphenylenediamine and aniline black, photo developers such as hydroquinone and para-amido-phenol, antioxidants such as hexamethylene tetramine, and synthetic and natural resins such as wood rosin and phenol formaldehyde, and detergents and constituents of rubber and latex gloves Other agents that cause contact dermatitis include, for example, metals (e.g. nickel, chromium, cobalt, including exposure during body piercing), latex, fragrances, chemicals, cosmetics, textiles, pesticides, plastics, pollen, and the like. Therapeutic agents such as drugs may also cause allergic contact dermatitis, particularly when administered topically or transdermally. Agents that cause non-allergic contact dermatitis include skin-irritating agents such as water, skin cleansers, industrial cleaning agents, alkalis, acids, oils, organic solvents, oxidizing agents, reducing agents, plant matter, animal matter, combinations thereof, and the like.

Another preferred skin condition is psoriasis. Psoriasis is a skin condition associated with hyper-proliferation of skin cells and immunologic involvement. Psoriasis is a common, idiopathic chronic skin disease characterized by inflamed, scaling, skin lesions containing infiltrates of neutrophils, lymphocytes, and monocytes. The compositions and methods of the present invention can be used to treat any form of psoriasis, including cutaneous, mucosal, ungual, and even psoriatic rheumatism. Compositions and methods of the present invention can be used to treat localized and generalized psoriasis.

One preferred embodiment of the invention provides prophylactic treatment to minimize skin sensitization produced by topical administration of therapeutic drugs. In another embodiment, the composition can be administered with the therapeutic drug or cosmetic. In still another embodiment, the composition is used for treatment after the reaction has occurred.

Another embodiment of the invention provides systemic administration of compositions to attenuate ongoing CD1d-restricted immune responses. This embodiment is preferable for any individual for whom activation of NKT cells would be adverse. Systemic conditions can include certain high risk spontaneously aborting pregnancies. It can also be used with autoimmune diseases such as lupus.

In another embodiment of the invention, a locally administrable topical cosmetic composition is provided, for example to provide hypoallergenic products.

The compositions of the present invention include those suitable for topical and systemic administration including oral, rectal, intravaginal, nasal, ophthalmic or parenteral administration, all of which may be used as routes of administration using the materials of the present invention. A preferred route of administration is topical. The topical composition may be in the form of a pharmaceutical but it does not have to be. For example, it can be a cosmetic.

In one embodiment of the invention, the locally administrable topical composition is provided for the prevention or treatment of skin conditions associated with CD1d-restricted immune responses. The locally administrable topical composition includes a topical carrier.

The topical carrier, as noted above, is one which is generally suited to topical drug administration and includes any such materials known in the art. The topical carrier is selected so as to provide the composition in the desired form, e.g., as a liquid, lotion, cream, paste, gel, powder, or ointment, and may be comprised of a material of either naturally occurring or synthetic origin. It is essential that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like. The composition of the invention may also be administered in the form of a shampoo, in which case conventional components of such a formulation are included as well, e.g., surfactants, conditioners, viscosity modifying agents, humectants, and the like.

Particularly preferred formulations herein are colorless, odorless ointments, lotions, creams and gels.

Ointments are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (OW) emulsions, and include, for example, cetyl alcohol, glyceryl monostearate, lanolin and stearic acid. Preferred water-soluble ointment bases are prepared from polyethylene glycols of varying molecular weight (Remington: The Science and Practice of Pharmacy).

Lotions are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose or sodium carboxymethyl-cellulose, or the like. A particularly preferred lotion formulation for use in conjunction with the present invention contains propylene glycol mixed with a hydrophilic petrolatum such as that which may be obtained under the trademark Aquaphor® from Beiersdorf, Inc. (Norwalk, Conn.).

Creams containing the selected agent are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington, supra, is generally a nonionic, anionic, cationic or amphoteric surfactant.

Gels formulations are preferred for application to the scalp. As will be appreciated by those working in the field of topical drug formulation, gels are semisolid, suspension-type systems. Single-phase gels contain organic macromolecules distributed substantially uniformly throughout the carrier liquid, which is typically aqueous, but also, preferably, contain an alcohol and, optionally, an oil.

Shampoos may be formulated with the standard shampoo components, i.e., cleansing agents, thickening agents, and preservatives with the cleansing agent representing the primary ingredient, typically an anionic surfactant or a mixture of an anionic and an amphoteric surfactant.

Various additives, known to those skilled in the art, may be included in the topical formulations of the invention. For example, solvents may be used to solubilize certain drug substances. Other optional additives include skin permeation enhancers, opacifiers, anti-oxidants, gelling agents, thickening agents, stabilizers, and the like. Other agents may also be added, such as antimicrobial agents, antifungal agents, antibiotics and anti-inflammatory agents such as steroids.

In the preferred topical formulations of the invention, the active agent is present in an amount which is generally less than 10% by weight of the total composition, preferably less than about 1% by weight, and most preferably less than about 0.1% by weight.

The topical compositions of the invention may also be delivered to the skin using a time-release mechanism. For example, "transdermal"-type patches, wherein the CD1d activation-blocking composition is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. The particular polymeric adhesive selected will depend on the particular drug, vehicle, etc., i.e., the adhesive must be compatible with all components of the drug-containing composition. In an alternative embodiment, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the CD1d activation-blocking composition and to any other components of the composition, thus preventing loss of any components through the upper surface of the device. The backing layer may be either occlusive or nonocclusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage and prior to use, the laminated structure preferably includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Such devices may be fabricated using conventional techniques, known in the art, for example by casting a fluid admixture of adhesive, drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/vehicle mixture.

As with the topical formulations of the invention, CD1d activation blocking composition contained within the reservoirs of these laminated system may contain a number of components. In some cases, the blocking composition may be delivered "neat." i.e., in the absence of additional liquid. In most cases, however, the composition will be dissolved, dispersed or suspended in a suitable pharmaceutically acceptable vehicle, typically a solvent or gel. Other components which may be present include preservatives, stabilizers, surfactants, and the like.

Preferably, the topical formulations and the laminated delivery systems also contain a skin permeation enhancer. A skin permeation enhancer can be co-administered. Suitable enhancers are well know in the art and include, for example, dimethylsulfoxide (DMSO), dimethyl formamide (DMF), N,N-dimethylacetamide (DMA), decylmethylsulfoxide ($C_{10}$ MSO), $C_2$-$C_6$ alkanediols, and the 1-substituted azacycloheptan-2-ones, particularly 1-n-dodecylcyclazacycloheptan-2-one (available under the trademark Azone® from Whitby Research Incorporated, Richmond, Va.), alcohols, and the like.

The ointments, pastes, creams and gels also may contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The topical compositions according to this invention may also include one or more preservatives or bacteriostatic agents, e.g., methyl hydroxybenzoate, propyl hydroxybenzoate, chlorocresol, benzalkonium chlorides, and the like. The topical compositions also can contain other active ingredients such as antimicrobial agents, particularly antibiotics, anesthetics, analgesics, and antipruritic agents.

Antimicrobial agents that can be used in the topical administration of the present invention are those compatible with skin and soluble in solvents. In addition, antimicrobial agents are active against a broad spectrum of microorganisms, including but are not limited to, gram positive and gram negative bacteria, yeast, and mold. Examples of the antimicrobial agents include, but are not limited to, triclosan (5-chloro-2-(2,4-dichlorophenoxy) phenol which is also known as Irgasan™ DP 300 manufactured by Ciba-Geigy Corporation), hexetidine (5-amino-1,3-bis(2-ethylhexyl)-5-methyl-hexahydropyrimidine), chlorhexidine salts (salts of N,N''-Bis(4-chlorophenyl)-3,12-diimino-2,4,11,14-tetraazatetradecanediimidiamide), 2-bromo-2-nitropropane-1,3-diol, hexyresorcinol, benzalkonium chloride, cetylpyridinium chloride, alkylbenzyldimethylammonium chlorides, iodine, phenol derivatives, povidone-iodine (polyvinylpyrrolidinone-iodine), parabens, hydantoins (2,4-imidazolidinedione), hydantoins derivatives (derivatives of 2,4-imidazolidinedione), phenoxyethanol, cis isomer of 1-(3- chloroallyl)-3,5,6-triaza-1-azoniaadamantane chloride (quarternium-15 which is also known as Dowicil 200 manufactured by Dow Chemical Company), diazolidinyl urea, benzethonium chloride, methylbenzethonium chloride, and mixtures thereof. Examples of hyndantoin derivatives include, but are not limited to, dimethylol-5,5-dimethylhydantoin (glydant). Preferably, examples of the antimicrobial agents include triclosan, cis isomer of 1-(3-chloroallyl)-3,5, 6-triaza-1-azoniaadamantane chloride (quaternnium-15), hyndantoins, hyndantoin derivatives such as dimethylol-5, 5-dimethylhydantoin (glydant), and mixtures thereof.

The percentage of the antimicrobial agents in the composition is about 0.01 wt. % to about 10 wt. %, and preferably, about 0.01 wt. % to about 2 wt. %.

In one embodiment such as where a latex condom or diaphragm is to be used, the CD1d activation block compositions can be included in ointments, foams, and creams that can be used during sex. For example, they can be administered preferably prior to or just after sexual contact such as intercourse. One preferred composition would be a vaginal foam, including a spermicide, containing one of the compounds.

The topical compositions and drug delivery systems of the invention can be used in the prevention or treatment of the skin conditions identified above. When used in a preventive (prophylactic) method, susceptible skin can be treated prior to exposure or just after exposure but any visible lesions on areas known to be susceptible to such lesions are observed. In treating skin conditions, it will be recognized by those skilled in the art that the optimal quantity and spacing of individual dosages will be determined by the nature and extent of the condition being treated, the form, route and site of administration, and the particular individual undergoing treatment, and that such optimums can be determined by conventional techniques. It will also be appreciated by one skilled in the art that the optimal dosing regimen, i.e., the number of doses can be ascertained using conventional course of treatment determination tests. Generally, a dosing regimen will involve administration of the selected topical formulation at least once daily, and preferably one to four times daily, until the symptoms have subsided.

Systemic administration of a composition may be by oral, parenteral, sublingual, rectal such as suppository or enteral administration, or by pulmonary absorption. Parenteral administration may be by intravenous injection, subcutaneous injection, intramuscular injection, intra-arterial injection, intrathecal injection, intra peritoneal injection or direct injection or other administration to one or more specific sites. When long term administration by injection is necessary, venous access devices such as medi-ports, in-dwelling catheters, or automatic pumping mechanisms are also preferred wherein direct and immediate access is provided to the arteries in and around the heart and other major organs and organ systems.

Compositions may also be administered to the nasal passages as a spray. Arteries of the nasal area provide a rapid and efficient access to the bloodstream and immediate access to the pulmonary system. Access to the gastrointestinal tract, which can also rapidly introduce substances to the blood stream, can be gained using oral enema, or injectable forms of administration. Compositions may be administered as a bolus injection or spray, or administered sequentially over time (episodically) such as every two, four, six or eight hours, every day (QD) or every other day (QOD), or over longer periods of time such as weeks to months. Compositions may also be administered in a timed-release fashion such as by using slow-release resins and other timed or delayed release materials and devices.

Where systemic administration is desired, orally active compositions are preferred as oral administration is a convenient and economical mode of drug delivery. Oral compositions may be poorly absorbed through the gastrointestinal lining. Compounds which are poorly absorbed tend to be highly polar. Preferably, such compositions are designed to reduce or eliminate their polarity. This can be accomplished by known means such as formulating the oral composition with a complimentary reagent which neutralizes its polarity, or by modifying the compound with a neutralizing chemical group. Preferably, the molecular structure is similarly modified to withstand very low pH conditions and resist the enzymes of the gastric mucosa such as by neutralizing an ionic group, by covalently bonding an ionic interaction, or by stabilizing or removing a disulfide bond or other relatively labile bond.

Treatments to the patient may be therapeutic or prophylactic. Therapeutic treatment involves administration of one or more compositions of the invention to a patient suffering from one or more symptoms of the disorder. Relief and even partial relief from one or more symptoms can correspond to an increased life span or simply an increased quality of life. Further, treatments that alleviate a pathological symptom can allow for other treatments to be administered.

The term "compatible", as used herein, means that the components of the compositions are capable of being commingled with the CD1d blocking agents of the present invention, and with each other, in a manner such that does not substantially impair the desired efficacy.

Doses of the pharmaceutical compositions of the invention will vary depending on the subject and upon the particular route of administration used. Dosages can range from 0.1 to 100,000 µg/kg per day, more preferably 1 to 10,000 µg/kg. By way of an example only, an overall dose range of from about, for example, 1 microgram to about 300 micrograms might be used for human use. This dose can be delivered at periodic intervals based upon the composition.

EXAMPLES

Animals 8-12 week old female C57Bl/6 mice were purchased from Taconic Farms. Inc. (Germantown, N.Y.). The CD1d-null allele (generated in a 129×C57Bl/6 founder (25) (26) was backcrossed 7 generations into the C57Bl/6 strain. (15) Homozygous CD1d deficient mice were obtained from littermate pairings and used to generate heterozygote CD1d deficient and wild type controls. Breeding pairs of mice deficient for CD1d on the BALB/c background were purchased from Jackson Labs (Bar Harbor, Me.). The C57Bl/6 and BALB/c J 281 null mice were established by specific deletion of the J 281 gene segment (27) (28). All mouse experiments were approved and conducted under IACUC guidelines.

Reagents

Contact hapten, 4-ethoxymethylene-2-phenyl-2-phenyl-2-oxazolin-5-one (oxazolone) was purchased from SIGMA, GalCer [(2S,3S,4R)-1-O-(-D-galactopyranosyl)-2-(N-hexacosanoylamino)-1,3,4-octadecanetriol was kindly provided by Pharmaceutical Research Laboratories, Kirin Brewery, Gunma, Japan, and CD1d-binding antagonists Polyethylene glycol $(PEG)_{2000}$ dipalmitoyl-L-phosphatidylethanolamine (DPPE-PEG) and $(PEG)_{2000}$ ceramide were purchased from Northern Lipids, Inc.

Contact Hypersensitivity

Mice at least seven weeks of age were sensitized epicutaneously on day 0 with 70 µl of 4% 4-ethoxymethylene-2-phenyl-2-oxazolin-5-one (oxazolone, Sigma, St. Louis, Mo.) in acetone/olive oil (4/1) and challenged five days later on the right ear with 20 µl of 0.5% oxazolone or carrier only on the left ear. The hapten-specific increase in ear thickness at 24 hours was determined with a micrometer. For experiments using DPPE-PEG, 4% oxazolone in acetone/olive oil (4/1) solutions with or without DPPE-PEG (in dosages ranging from 5 mg/ml to 100 mg/ml) were applied. Finally, a mixture off 0.5% oxazolone and 50 mg/ml DPPE-PEG was used for the inhibition of oxazalone recall.

Analysis of invariant Vα14Jα281 TCR frequency. Total RNA was isolated from spleens of individual mice using TRIZOL (Gibro BRL, Grand Island, N.Y.) according to the manufacturer's recommendations. First-strand cDNA synthesis was performed using oligo(dT) as a primer for reverse transcription of 2 µg of total RNA in a 50 µl reaction mixture using MMLV-RT (Life Technologies, GIBCO-BRL, Gaithersgurg, Mass.). Quantitative analysis of Vα14Jα281 T cell frequency was done using multiplex RT-PCR by comparing the intensity of the TCR α-chain CDR3 band with the invariant INKT cell specific band, as previously described (29).

Treatment Protocols

Mice received a series of 5 intraperitoneal injections of either 2 µg of αManCer (2 µg i.p. diluted in a solution of phosphate buffered saline and 0.5% Tween-20 every other day, starting 3 days prior to skin sensitization and continuing through to re-challenge.

Statistical Analysis

Significant differences between groups were evaluated with a Mann-Whitney test, or where appropriate, a two tailed Student's t test. Mean differences were considered significant when $p<0.05$.

Contact hypersensitivity is ablated both in CD1d knock out and in iNKT cell-deficient Jα281 knock out mice. Mice were sensitized epicutaneously on day 0 with oxazolone and challenged six days later on the ear with oxazolone or carrier only, as described above. The hapten-specific increase in ear thickness at 24 hours was determined with a micrometer. (See FIG. 1).

To examine the functional importance of CD1d restricted iNKT cells in CHS we measured the ability of iNKT cell-deficient mice to generate contact hypersensitivity to oxazolone. This reaction is a form of delayed-type hypersensitivity in which hapten-protein conjugates are presented by cutaneous dendritic cells, followed by their migration to regional lymph nodes, to hapten-specific CD4 and CD8 positive T lymphocytes (1)'(2)'(30)'(3). Upon secondary hapten challenge, sensitized T cells initiate a local inflammatory response. In this system, activation of iNKT cells by CD1d on skin DC is thought to be an important initiation step followed by the elaboration of cytokines such as IL-4 (10) (31). Interestingly, contact hypersensitivity to oxazolone was significantly impaired in INKT cell-deficient mice on both the C57B1/6 and Balb/c backgrounds (FIG. 1), revealing a requirement for CD1d-restricted T cells for maximal hapten-specific immunity.

Figure 2:
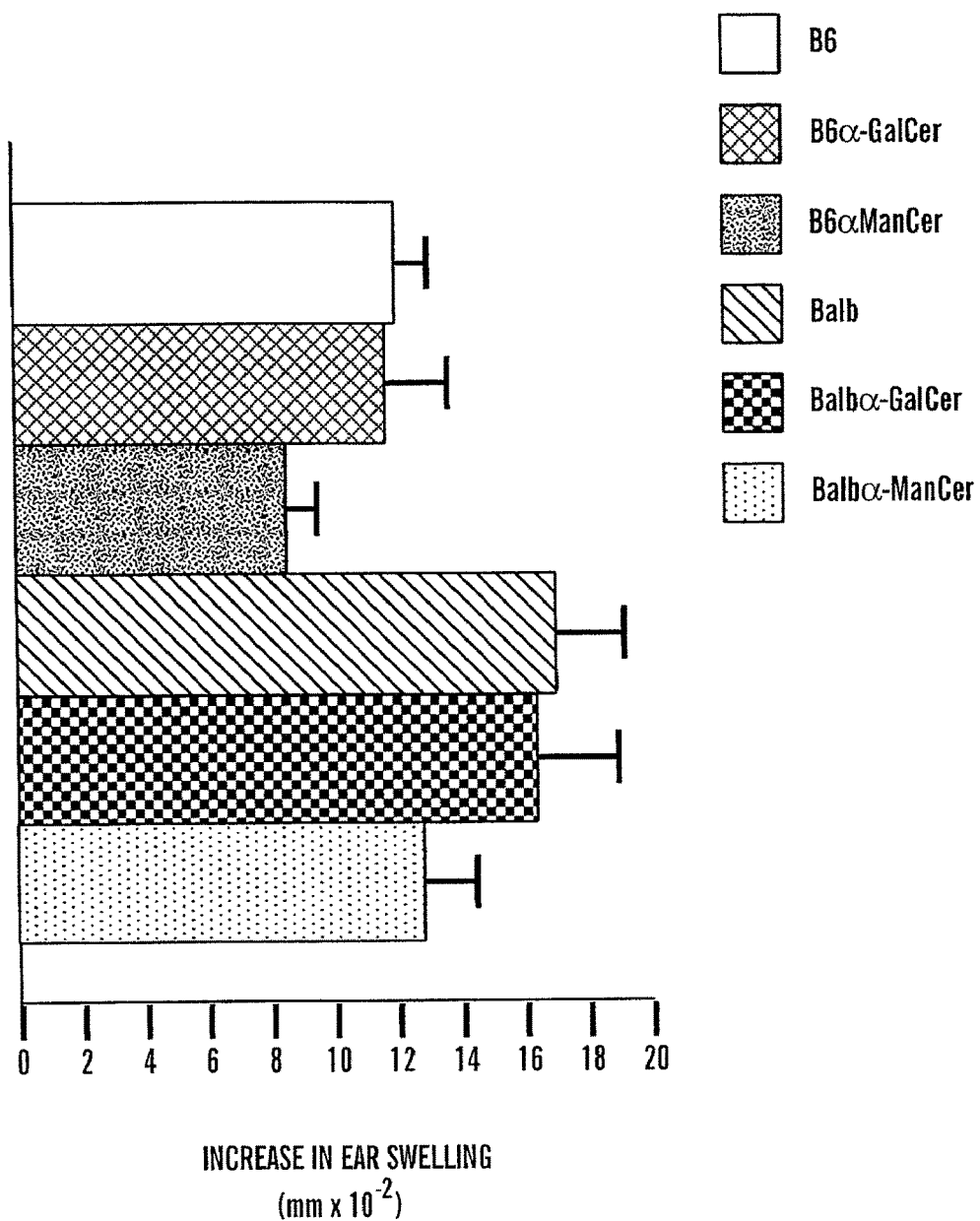
FIG. 2 is a graph showing that systemic treatment with α-ManCer inhibited oxazolone-induced contact hypersensitivity. Mice at least seven weeks of age were sensitized epicutaneously on day 0 with 70 µl of 4% oxazolone in acetone/olive oil (4/1) with or without treatment with α-Gal-Cer or α-ManCer. The hapten specific increase in ear thickness at 24 hours was determined using a micrometer. 5 days later the right ear was challenged with 0.5% oxazolone, 10 µl on each side or carrier only. The hapten specific increase in ear thickness at 24 hours was determined using a micrometer.

Systemical administration of an inactive CD1d binding lipid, α-ManCer inhibits contact hypersensitivity to oxazolone. Since CD1d- or Jα281-null mice had impaired CSH responses, we examined whether activation or inhibition of iNKT cells with the protypic CD1d-dependent glycolipid agonist α-GalCer or antagonist α-ManCer, a glycolipid that is known to bind CD1d but fails to activate iNKT cells, would modulate CSH responses. Mice were treated with the α-GalCer or α-ManCer by i.p. injections administered prior to and during the sensitization phase with oxazolone. Pretreatment of mice with α-ManCer inhibited the CSH response by 50% when compared to the control group (FIG. 2). Conversely, administration of α-GalCer did not alter the CSH response to oxazolone. Thus, CHS responses were not augmented by iNKT cell activation, but could be significantly inhibited by systemic treatment with CD1d antagonists previously demonstrated not to activate iNKT cells in vivo and in vitro.

Figure 3:
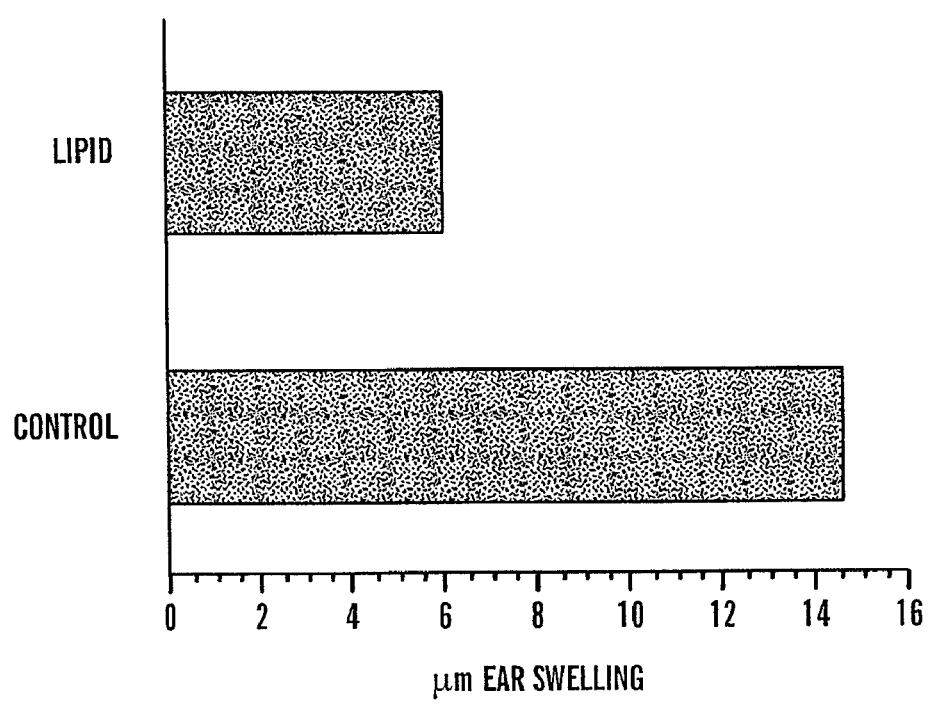
FIG. 3 is a graph showing that topical DPPE-PEG (a CD1d-binding lipid) inhibits oxazolone-induced contact hypersensitivity. Mice at least seven weeks of age were sensitized epicutaneously on day 0 with 70 1 of 4% 4-ethoxymethylene-2-phenyl-2-oxazolin-5-one (oxazolone, Sigma) in acetone/olive oil (4/1) with or without DPPE-PEG (100 mg/ml) and challenged five days later on the ear with 20 1 of 0.5% oxazolone or carrier only. The hapten-specific increase in ear thickness at 24 hours was determined with a micrometer.

Topical DPPE-PEG (a CD1d-binding lipid) inhibits oxazolone-induced contact hypersensitivity (FIG. 3). Mice were sensitized epicutaneously on day 0 with oxazolone with or without DPPE-PEG (100 mg/ml) and challenged five days later on the ear with oxazolone or carrier only, as described above. The hapten-specific increase in ear thickness at 24 hours was determined with a micrometer.

Figure 4A:
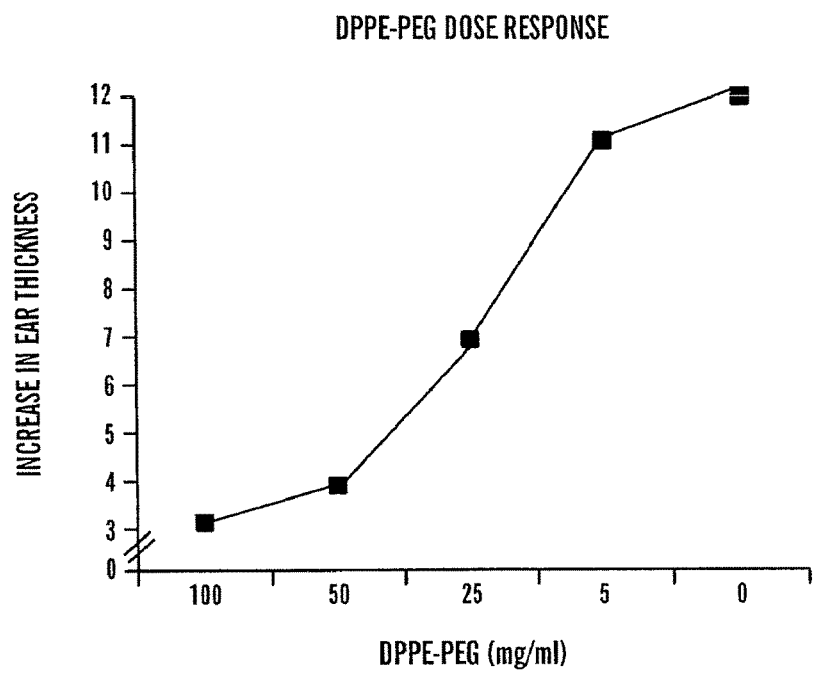
FIG. 4A is a dose response curve showing that topical administration of DPPE-PEG inhibits oxazolone-induced contact hypersensitivity in a dose dependent fashion. Mice at least seven weeks of age were sensitized epicutaneously on day 0 with 70 1 of 4% oxazolone in acetone/olive oil (4/1) with DPPE-PEG in a series of increasing dosage, ranging from 0 to 100 mg/ml. 5 days later the right ear was challenged with 0.5% oxazolone, 10 1 on each side or carrier only. The hapten specific increase in ear thickness at 24 hours was determined using a micrometer.

Topical administration of iNKT antagonist lipids inhibited the generation of CHS. Increasing doses of DPPE-PEG inhibit oxazolone-induced hypersensitivity in a dose-dependent manner, as shown in FIG. 4A. We evaluated whether administration of CD1d antagonists could be used topically to block the generation of CSH responses. Since a synthetically modified lipid, DPPE-PEG, was recently demonstrated to be a significantly more soluble and effective competitor of α-GalCer presentation than α-ManCer and was available in pharmacologic quantities, (22) this reagent was chosen for use as a topical inhibitor of CSH. In control experiments systemic administration of DPPE-PEG or PEG-ceramide inhibited CHS as effectively as α-ManCer (data not shown). For these experiments, wild type C57B1/6 mice were sensitized with oxazolone mice in the presence of increasing doses of DPPE-PEG. Half-maximal inhibition of CSH was achieved at 25 mg/ml of DPPE-PEG (FIG. 4A) and CSH could was inhibited in a dose response fashion.

Figure 4B:
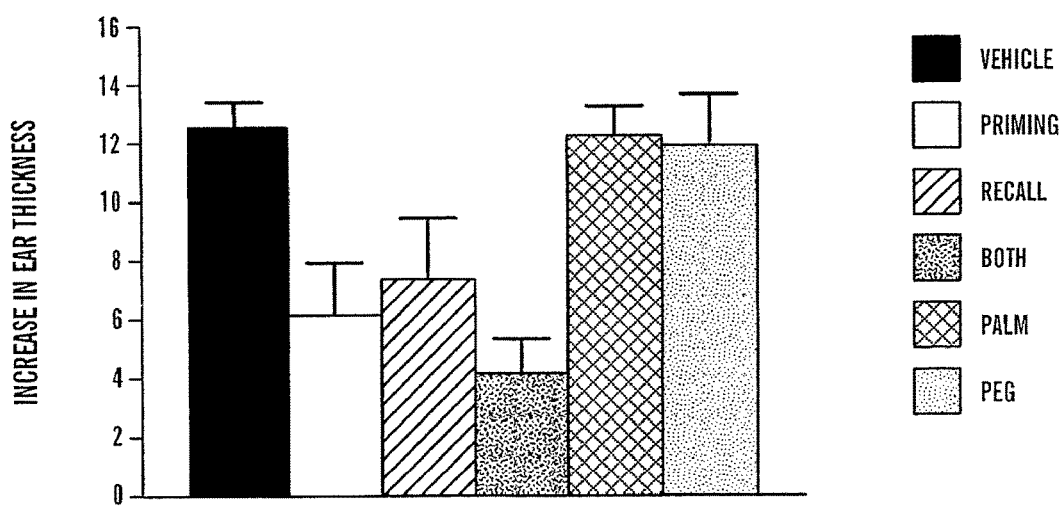
FIG. 4B is a graph showing topical administration of DPPE-PEG inhibits oxazolone-induced contact hypersensitivity both during recall and priming. Mice at least seven weeks of age were sensitized epicutaneously on day 0 with 70 1 of 4% oxazolone in acetone/olive oil (4/1) with or without DPPE-PEG. 5 days later the right ear was challenged with 0.5% oxazolone, 10 1 on each side or carrier only. One group that was primed with oxazolone only was challenged with a mixture of oxazolone 0.05% and DPPE-PEG (100 mg/ml). The hapten specific increase in ear thickness at 24 hours was determined using a micrometer.

FIG. 4B shows that topical DPPE-PEG inhibits contact hypersensitivity during recall and priming. Inclusion of DPPE-PEG can inhibit recall to oxazolone even after priming with the agent. To determine whether the inhibitory effect of DPPE-PEG was dependent on when the inhibitor was used, oxazolone-induced CSH responses were tested when DPPE-PEG was present at both phases, or only during priming or recall. Contact hypersensitivity responses were maximally inhibited by the inclusion of DPPE-PEG during both the challenge and recall portions of the experiment (FIG. 4B). Notably, the CSH responses were also inhibited, but to a lesser extent, when the reagent was used only during the challenge or recall phases of the response. Importantly, the effect was specific for DPPE-PEG since neither palmitic acid, nor PEG alone were effective inhibitors of CSH (FIG. 2 and data not shown).

Figure 5:
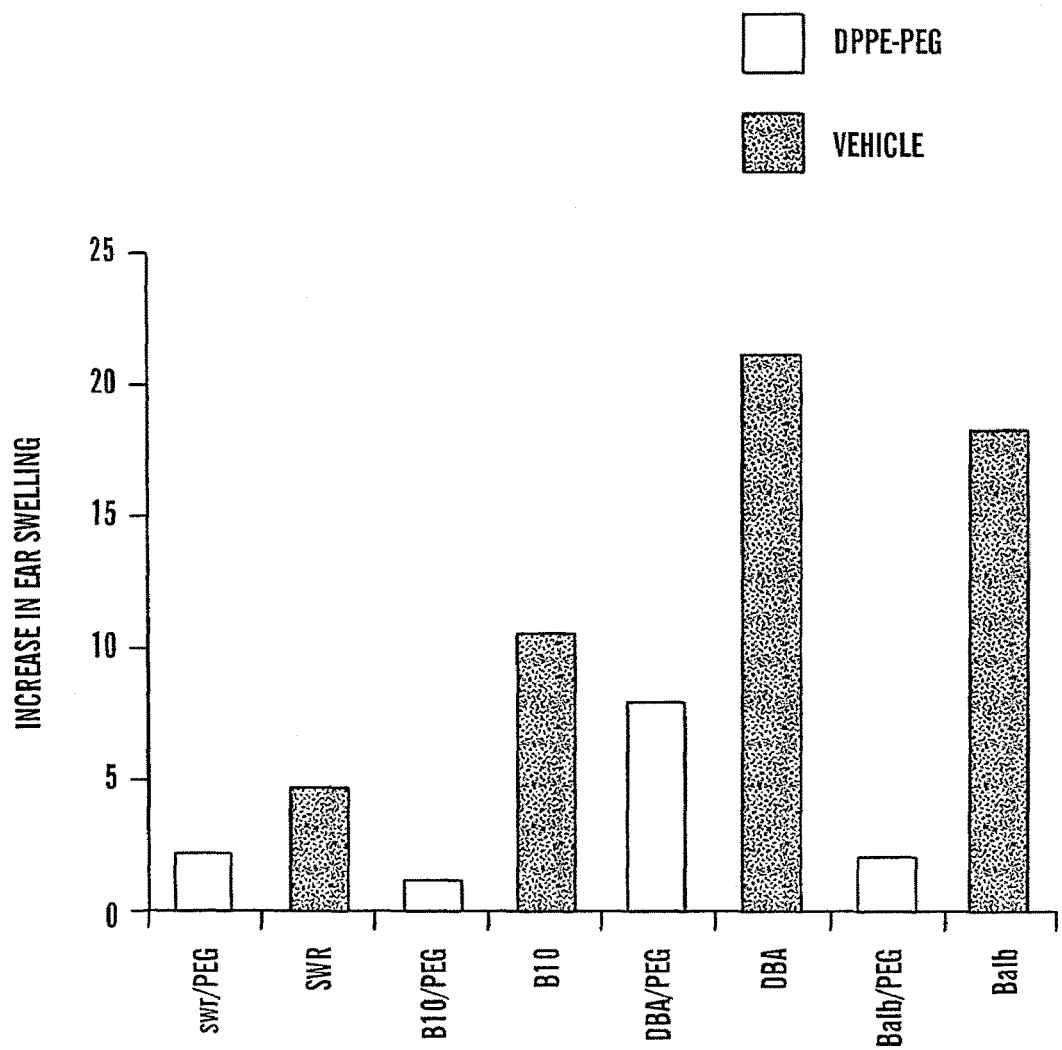
FIG. 5 is a graph showing that inhibition of CSH by DPPE-PEG was independent of MHC alleles. In bred strains of mice with unrelated MHC alleles were challenged with oxazolone with or without DPPE-PEG at 100 mg/ml as described for FIG. 4. The application of antagonist lipid inhibited CHS responses in SWR, C57B1/10, DBA, and BALB/c mice.

Inhibition of CSH by DPPE-PEG is strain independent (FIG. 5). The CD1d antigen presentation system can respond rapidly to cues in the environment and this function has been conserved since the evolutionary divergence of rodents and humans (32) (24). To test whether the effect of DPPE-PEG was MHC or strain dependent, oxazalone-induced CSH was determined for 4 additional MHC-unrelated congenic mouse strains in the presence or absence of the inhibitor. The addition of DPPE-PEG was an effective inhibitor in all strains tested (FIG. 5). There was, however, significant strain variability in both the magnitude of the responses to oxazolone and the ability of DPPE-PEG to inhibit CSH. Therefore, DPPE-PEG was an effective inhibitor of oxazolone-induced CSH in a MHC-independent fashion and in all strains tested.

CSH reactions were inhibited in mice deficient in iNKT cells directly confirming an important role for iNKT cells in CSH. Furthermore, CHS was specifically inhibited in those mice that were treated with CD1d-binding antagonists. Thus, blockade of the CD1d system could be used to treat ACD in an antigen- and MHC-independent fashion.

REFERENCES

1. Eisen, H. N., L. Orris, and S. Belman. 1952. Elicitation of delayed allergic skin reactions with haptens: the dependence of elicitation on hapten combination with protein. *Journal of Experimental Medicine* 95:473.
2. Silberberg, I., R. L. Baer, and S. A. Rosenthal. 1976. The role of Langerhans cells in allergic contact hypersensitivity. A review of findings in man and guinea pigs. *J Invest Dermatol* 66, no. 4:210.
3. Gocinski, B. L., and R. E. Tigelaar. 1990. Roles of CD4+ and CD8+ T cells in murine contact sensitivity revealed by in vivo monoclonal antibody depletion. *J Immunol* 144, no. 11:4121.
4. Dieli, F., M. Taniguchi, G. L. Asherson, G. Sireci, N. Caccamo, E. Scire, C. T. Bonanno, and A. Salerno. 1998. Development of hapten-induced IL-4-producing CD4+ T lymphocytes requires early IL-4 production by alphabeta T lymphocytes carrying invariant V(alpha)14 TCR alpha chains. *Int Immunol* 10, no. 4:413.
5. Ptak, W., and P. W. Askenase. 1992. Gamma delta T cells assist alpha beta T cells in adoptive transfer of contact sensitivity. *J Immunol* 149, no. 11:3503.
6. Yokozeki, H., K. Watanabe, K. Igawa, Y. Miyazaki, I. Katayama, and K. Nishioka. 2001. Gammadelta T cells assist alphabeta T cells in the adoptive transfer of contact hypersensitivity to para-phenylenediamine. *Clin Exp Immunol* 125, no. 3:351.
7. Medzhitov, R., and C. Janeway, Jr. 2000. Innate immune recognition: mechanisms and pathways. *Immunol Rev* 173:89.
8. Watanabe, N., K. Ikuta, S. Fagarasan, S. Yazumi, T. Chiba, and T. Honjo. 2000. Migration and differentiation of autoreactive B-1 cells induced by activated gamma/delta T cells in antierythrocyte immunoglobulin transgenic mice. *J Exp Med* 192, no. 11:1577.
9. Ishii, N., K. Takahashi, H. Nakajima, S. Tanaka, and P. W. Askenase. 1994. DNFB contact sensitivity (C S) in BALB/c and C3H/He mice: requirement for early-occurring, early-acting, antigen-specific, C S-initiating cells with an unusual phenotype (Thy-1+, CD5+, CD3–, CD4–, CD8–, sIg–, B220+, MHC class II–, CD23+, IL-2R–, IL-3R+, Mel-14–, Pgp-1+, J11d+, MAC-1+, LFA-1+, and Fc gamma RII+). *J Invest Dermatol* 102, no. 3:321.
10. Askenase, P. W. 2001. Yes T cells, but three different T cells (alphabeta, gammadelta and N K T cells), and also B-1 cells mediate contact sensitivity. *Clin Exp Immunol* 125, no. 3:345.
11. Porcelli, S. A., and R. L. Modlin. 1999. The CD1 system: antigen-presenting molecules for T cell recognition of lipids and glycolipids. *Annu Rev Immunol* 17:297.
12. Godfrey, D. I., K. J. Hammond, L. D. Poulton, M. J. Smyth, and A. G. Baxter. 2000. NKT cells: facts, functions and fallacies. *Immunol Today* 21, no. 11:573.
13. Baxter, A. G., S. J. Kinder, K. J. L. Hammond, R. Scollay, and D. I. Godfrey. 1997. Association between αβTCR+CD4–CD8– T-cell deficiency and IDDM in NOD/Lt mice. *Diabetes* 46:572.
14. Wilson, S. B., S. C. Kent, K. T. Patton, T. Orban, R. A. Jackson, M. Exley, S. Porcelli, D. A. Schatz, M. A. Atkinson, S. P. Balk, J. L. Strominger, and D. A. Hafler. 1998. Extreme Th1 bias of invariant Valpha24JalphaQ T cells in type 1 diabetes. *Nature* 391, no. 6663:177.
15. Naumov, Y. N., K. S. Bahjat, R. Gausling, R. Abraham, M. A. Exley, Y. Koezuka, S. B. Balk, J. L. Strominger, M. Clare-Salzer, and S. B. Wilson. 2001. Activation of CD1d-restricted T cells protects NOD mice from developing diabetes by regulating dendritic cell subsets. *Proc Natl Acad Sci USA* 98, no. 24:13838.
16. Cui, J., T. Shin, T. Kawano, H. Sato, E. Kondo, I. Toura, Y. Kaneko, H. Koseki, M. Kanno, and M. Taniguchi. 1997. Requirement for Vα14 NKT cells in IL-12-mediated rejection of tumors. *Science* 278:1623.
17. Smyth, M. J., K. Y. T. Thia, S. E. A. Street, E. Cretney, J. A. Trapani, M. Taniguchi, K. Tetsu, S. B. Pelikan, N. Y. Crowe, and D. I. Godfrey. 2000. Differential Tumor Surveillance by Natural Killer (N K) and NKT Cells. *J. Exp. Med.* 191, no. 4:661.
18. Kitamura, H., K. Iwakabe, T. Yahata, S. Nishimura, A. Ohta, Y. Ohmi, M. Sato, K. Takeda, K. Okumura, L. Van Kaer, T. Kawano, M. Taniguchi, and T. Nishimura. 1999. The natural killer T (NKT) cell ligand alpha-galactosyl-ceramide demonstrates its immunopotentiating effect by inducing interleukin (IL)-12 production by dendritic cells and IL-12 receptor expression on NKT cells. *J Exp Med* 189, no. 7:1121.
19. Tomura, M., W.-G. Yu, H.-J. Ahn, M. Yamashita, Y.-F. Yang, S. Ono, T. Hamaoka, T. Kawano, M. Taniguchi, Y. Koezuka, and H. Fujiwara. 1999. A Novel Function of Valpha14+CD4+NKT Cells: Stimulation of IL-12 Production by Antigen-Presenting Cells in the Innate Immune System. *J. Immunol* 163:93.
20. Toura, I., T. Kawano, Y. Akutsu, T. Nakayama, T. Ochiai, and M. Taniguchi. 1999. Cutting edge: inhibition of experimental tumor metastasis by dendritic cells pulsed with alpha-galactosylceramide. *J Immunol* 163, no. 5:2387.
21. Zeng, Z.-H., A. R. Castano, B. W. Segelke, E. A. Stura, P. A. Peterson, and I. A. Wilson. 1997. Crystal structure of mouse CD1:an MHC-like fold with a large hydrophobic binding groove. *Science* 277, no. 5324:339.
22. Naidenko, O. V., J. K. Maher, W. A. Ernst, T. Sakai, R. L. Modllin, and M. Kronenberg. 1999. Binding and Antigen Presentation of Ceramide-containing glycolipids by Soluble Mouse and Human CD1d Molecules. *J. Exp. Med.* 190, no. 8:1069.
23. Joyce, S., A. S. Woods, J. W. Yewdell, J. R. Bennink, A. D. De Silva, A. Boesteanu, S. P. Balk, R. J. Cotter, and R. R. Brutkiewicz. 1998. Natural ligand of mouse CD1d1: cellular glycosylphosphatidylinositol. *Science* 279, no. 5356:1541.
24. Brossay, L., and M. Kronenberg. 1999. Highly conserved antigen-presenting function of CD1d molecules. *Immunogenetics* 50, no. 3-4:146.
25. Sonoda, K. H., M. Exley, S. Snapper, S. P. Balk, and J. Stein-Streilein. 1999. CD1-reactive natural killer T cells are required for development of systemic tolerance through an immune-privileged site [see comments]. *J Exp Med* 190, no. 9:1215.
26. Exley, M. A., N. J. Bigley, O. Cheng, S. M. Tahir, S. T. Smiley, Q. L. Carter, H. F. Stills, M. J. Grusby, Y. Koezuka, M. Taniguchi, and S. P. Balk. 2001. CD1d-reactive T-cell activation leads to amelioration of disease caused by diabetogenic encephalomyocarditis virus. *J Leukoc Biol* 69, no. 5:713.

27. Smiley, S. T., M. H. Kaplan, and M. J. Grusby. 1997. Immunoglobulin E production in the absence of interleukin-4-secreting CD1-dependent cells. *Science* 275:977.
28. Kawano, T., J. Cui, Y. Koezuka, I. Toura, Y. Kaneko, K. Motoki, H. Ueno, R. Nakagawa, H. Sato, E. Kondo, H. Koseki, and M. Taniguchi. 1997. *CD*1d-restricted and TCR-mediated activation of valpha14 NKT cells by glycoceramides. *Science* 278:1626.
29. Gorski, J., M. Yassai, X. Zhu, B. Kissela, B. Kissella, C. Keever, and N. Flomenberg. 1994. Circulating T cell repertoire complexity in normal individuals and bone marrow recipients analyzed by CDR3 size spectratyping. Correlation with immune status. *J Immunol* 152, no. 10:5109.
30. Bacci, S., P. Alard, R. Dai, T. Nakamura, and J. W. Streilein. 1997. High and low doses of haptens dictate whether dermal or epidermal antigen-presenting cells promote contact hypersensitivity. *Eur J Immunol* 27, no. 2:442.
31. Gerlini, G., H. P. Hefti, M. Kleinhans, B. J. Nickoloff, G. Burg, and F. O. Nestle. 2001. Cd1d is expressed on dermal dendritic cells and monocyte-derived dendritic cells. *J Invest Dermatol* 117, no. 3:576.
32. Bendelac, A., M. N. Rivera, H.-S. Park, and J. H. Roark. 1997. Mouse CD1-Specific NK1 T Cells: Development, Specificity, and Function. *Annual Review of Immunology* 15:535.
33. Hopkin, J. M. 1997. Mechanisms of enhanced prevalence of asthma and atopy in developed countries. *Curr Opin Immunol* 9, no. 6:788.
34. Akdis, C. A., M. Akdis, A. Trautmann, and K. Blaser. 2000. Immune regulation in atopic dermatitis. *Curr Opin Immunol* 12, no. 6:641.
35. Girolomoni, G., S. Sebastiani, C. Albanesi, and A. Cavani. 2001. T-cell subpopulations in the development of atopic and contact allergy. *Curr Opin Immunol* 13, no. 6:733.
36. Apostolou, I., Y. Takahama, C. Belmant, T. Kawano, M. Huerre, G. Marchal, J. Cui, M. Taniguchi, H. Nakauchi, J. J. Fournie, P. Kourilsky, and G. Gachelin. 1999. Murine natural killer T(NKT) cells [correction of natural killer cells] contribute to the granulomatous reaction caused by mycobacterial cell walls. *Proc Natl Acad Sci USA* 96, no. 9:5141.
37. Mempel, M., B. Flageul, F. Suarez, C. Ronet, L. Dubertret, P. Kourilsky, G. Gachelin, and P. Musette. 2000. Comparison of the T cell patterns in leprous and cutaneous sarcoid granulomas. Presence of Valpha24-invariant natural killer T cells in T-cell-reactive leprosy together with a highly biased T cell receptor Valpha repertoire. *Am J Pathol* 157, no. 2:509.
38. Mempel, M., C. Ronet, F. Suarez, M. Gilleron, G. Puzo, L. Van Kaer, A. Lehuen, P. Kourilsky, and G. Gachelin. 2002. Natural Killer T Cells Restricted by the Monomorphic MHC Class Ib CD1d1 Molecules Behave Like Inflammatory Cells. *Journal of mnmunology* 168:365.
39. Sebastiani, S., P. Allavena, C. Albanesi, F. Nasorri, G. Bianchi, C. Traidl, S. Sozzani, G. Girolomoni, and A. Cavani. 2001. Chemokine receptor expression and function in CD4+ T lymphocytes with regulatory activity. *J Immunol* 166, no. 2:996.
40. Cavani, A., F. Nasorri, C. Prezzi, S. Sebastiani, C. Albanesi, and G. Girolomoni. 2000. Human CD4+ T lymphocytes with remarkable regulatory functions on dendritic cells and nickel-specific Th1 immune responses. *J Invest Dermatol* 114, no. 2:295.
41. Bendelac, A., R. D. Hunziker, and O. Lantz. 1996. Increased interleukin 4 and immunogloulin E production in transgenic mice overexpressing NK1 T cells. *Journal of Experimental Medicine* 184:1285.
42. Mendiratta, S. K., W. D. Martin, S. Hong, A. Boesteanu, S. Joyce, and L. Van Kaer. 1997. CD1d1 mutant mice are deficient in natural T cells that promptly produce IL-4. *Immunity* 6:469.
43. Wilson, S. B., S. C. Kent, H. F. Horton, A. A. Hill, P. L. Bollyky, D. A. Hafler, J. L. Strominger, and M. C. Byrne. 2000. Multiple differences in gene expression in regulatory Valpha24JalphaQ T cells from identical twins discordant for type I diabetes. *Proc Natl Acad Sci USA* 97, no. 13:7411.
44. Yang, O. O., F. K. Racke, P. T. Nguyen, R. Gausling, M. E. Severino, H. F. Horton, M. C. Byrne, J. L. Strominger, and S. B. Wilson. 2000. CD1d on Myeloid Dendritic Cells Stimulates Cytokine Secretion and Cytolytic Activity of Valpha24JalphaQ T Cells: A Feedback Mechanism for Immune Regulation. *J. Immunol.* 165, no. 7:3756.
45. Exley, M., J. Garcia, S. P. Balk, and S. Porcelli. 1997. Requirements for CD1d Recognition by Human Invariant Vα24+CD4−CD8− T Cells. *The Journal of Experimental Medicine* 186:1.
46. Kadowaki, N., S. Antonenko, S. Ho, M. C. Rissoan, V. Soumelis, S. A. Porcelli, L. L. Lanier, and Y. J. Liu. 2001. Distinct cytokine profiles of neonatal natural killer t cells after expansion with subsets of dendritic cells. *J Exp Med* 193, no. 10:1221.
47. Ikarashi, Y., R. Mikami, A. Bendelac, M. Terme, N. Chaput, M. Terada, T. Turz, E. Angevin, F. A. Lemonnier, H. Wakasugi, and L. Zitvogel. 2001. Dendritic Cell Maturation Overrules H-2D-mediated Natural Killer T (NKT) Cell Inhibition: Critical Role for B7 in CD1d-dependent NKT Cell Interferon gamma Production. *Journal of Experimental Medicine* 194, no. 8:1179.
48. Rissoan, M. C., V. Soumelis, N. Kadowaki, G. Grouard, F. Briere, R. de Waal Malefyt, and Y. J. Liu. 1999. Reciprocal control of T helper cell and dendritic cell differentiation [see comments]. *Science* 283, no. 5405:1183.
49. Shreedhar, V., A. M. Moodycliffe, S. E. Ullrich, C. Bucana, M. L. Kripke, and L. Flores-Romo. 1999. Dendritic cells require T cells for functional maturation in vivo. *Immunity* 11, no. 5:625.

All references described herein are incorporated herein by reference.

What is claimed is:
1. A composition formulated for topical administration comprising:
   (a) an agent that attenuates CD1d-restricted NK T cell responses, wherein 1) the agent is a phospholipid conjugated to polyethylene glycol (PEG) that binds CD1d and i) inhibits activation of CD1d-restricted NK T cells or ii) blocks CD1d-specific receptors, 2) the phospholipid is 1,2-Dipalmitoyl-sn-Glycero-3-Phosphoethanolamine (DPPE), and 3) the DPPE is present in an amount greater than 2.5% weight per volume; and
   (b) a carrier for topical administration, wherein the carrier is a vegetable oil.
2. The composition of claim 1, wherein the agent is present in an amount between 2.5% weight per volume and 10.0% weight per volume.

3. The composition of claim 1, wherein the agent is 1,2-Dipalmitoyl-sn-Glycero-3-Phosphoethanolamine-N-[Poly (ethylene glycol) 2000] (DPPE-PEG).

* * * * *

UNITED STATES PATENT AND TRADEMARK OFFICE
CERTIFICATE OF CORRECTION

PATENT NO. : 10,226,476 B2
APPLICATION NO. : 14/802893
DATED : March 12, 2019
INVENTOR(S) : S. Brian Wilson et al.

Page 1 of 1

It is certified that error appears in the above-identified patent and that said Letters Patent is hereby corrected as shown below:

In the Specification

Column 1, Line 15, replace:
"This invention was supported by National Institutes of Health Grants R01 A145051, K11 DK02345, and R01 CA74886 and the government of the United States has certain rights thereto."

Should read:
-- This invention was made with government support under grant number CA074886 awarded by The National Institutes of Health. The government has certain rights in the invention. --

Signed and Sealed this
Twelfth Day of November, 2019

Andrei Iancu
*Director of the United States Patent and Trademark Office*